(12) United States Patent
Simmons et al.

(10) Patent No.: US 6,563,020 B1
(45) Date of Patent: May 13, 2003

(54) MAIZE CHITINASES AND THEIR USE IN ENHANCING DISEASE RESISTANCE IN CROP PLANTS

(75) Inventors: Carl R. Simmons, Des Moines, IA (US); Nasser Yalpani, Johnston, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/522,714

(22) Filed: Mar. 10, 2000

Related U.S. Application Data
(60) Provisional application No. 60/125,915, filed on Mar. 24, 1999.

(51) Int. Cl.$^7$ .............................. A01H 5/00; A01H 5/10; C12N 5/04; C12N 5/10; C12N 15/29; C12N 15/56; C12N 15/82

(52) U.S. Cl. ...................... 800/279; 800/286; 800/298; 800/320.1; 800/312; 800/322; 800/306; 800/320.2; 800/320.3; 800/320; 800/314; 435/418; 435/419; 435/412; 435/415; 435/416; 435/200; 536/23.6; 536/23.2

(58) Field of Search ............................. 536/23.7, 23.6; 800/278, 322, 279, 312, 298, 306, 320.1, 314, 320.3, 300, 320.2, 286; 435/418, 419, 412, 415, 416, 200

(56) References Cited

U.S. PATENT DOCUMENTS

| | | |
|---|---|---|
| 4,940,840 A | 7/1990 | Suslow et al. |
| 5,539,095 A | 7/1996 | Sticklen et al. |
| 5,633,450 A | 5/1997 | Suslow et al. |
| 5,670,706 A | 9/1997 | Cornelissen et al. |
| 5,728,382 A | 3/1998 | Sticklen et al. |
| 5,932,698 A | 8/1999 | Dubois et al. |

FOREIGN PATENT DOCUMENTS

| | | |
|---|---|---|
| CA | 2110764 | 6/1995 |
| EP | 0 440 304 A1 | 7/1991 |
| WO | WO92/20807 | 11/1992 |
| WO | WO95/02319 | 1/1995 |

OTHER PUBLICATIONS

Swapan K. Datta etal., Pathogenesis—Related Proteins in Plants Libary of Congress Card No. –99–12438 p. 77–98.*
Jaap J. Beintema, Structural features of plant chitinases and chitin—binding proteins Department of Biochemistry, Rijksuniversiteit Groningen, Nijenborgh 4, 9747 AG Gronongen the Netherlands p. 159–163.*
A. Mora, E. D. Earle, Combination of Trichoderma harzianum edochitinase and a membrane—affecting fungicide on control Alternaria leaf spot in transgenic broccoli plants Received: May 9, 2000/ revised: Aug. 7, 2000/ Published online : Feb. 2,2001.*

Karabi Datta etal., Enhanced resistance to sheath blight by constitutive expression of infection—related rice chitinase in transgenic elite indica rice cultivars, Plant Science 160 (2001) p. 405–414.*
Klaus H. Oldach et al., Heterologous Expression of Genes Mediating Enhanced Fungal Resistance in Transgenic Wheat MPMI vol. 14, No. 7, 2001, p. 832–838, Publication No. M–2001–0508–01R. 2001 The American Phytopathological Society.*
Escott et al., Inducible chitinolytic system of *Aspergillus fumigatus*, 1998, Microbiology, vol. 144, pp. 1575–1581.*
Sowka et al., Indetification and Cloning of Prs a 1, a 32–kDa Endochitinase and Major Allergen of Avocado, and Its Expression in the Yeast *Pichia pastoris*, Oct. 1998, The Journal of Biological, vol. 273, pp. 28091–28097.*
Sakai et al., Purfication and Characterization of Three Thermostable Endochitinases of a . . . , Sep. 1988, Applied and Enviromental Microbiology, vol. 64, No. 9, pp. 3397–3402.*
Herrera–Estrella et al., Chitinases in biological control, 1999.*
Nagasaki et al., "Rice Class III Chitinase Homologues Isolated by Random Cloning of Rice cDNAs" 1997, DNA Research vol. 4, pp. 379–385.*
Lazar et al., "Transforming Growth Factor x: Mutation of Aspartic Acid 47 and Leucine 48 Results in Different Biological Activities", Mar. 1988, Molecular and Cellular Biology vol. 8 No. 3, pp. 1247–1252.*
Neuhaus et al, "High–Level expression of a tobacco chitinase gene in *Nicotiana sylvestris*. Susceptibility of transgenic plants to *Cercospora nicotianae* infection", 1991, Plant Molecular Biology, vol. 16:, pp. 141–151.*
Bowie et al, Deciphering the Message in Protein Sequences: Tolerance to Amino Acid Substitutions, Mar. 1990, Science vol. 247, pp. 1306–1310.*
Hill et al, "Functional Analysis of Conserved Histidines in ADP–Glucose Pyrophosphorylase from *Escherichia coli*", 1998, Biochemical and Biophysical Research Communications vol. 244 pp. 573–577.*
Broun et al, "Catalytic Plasticity of Fatty Acid Modiciation Enzymes Underlying chemical Diversity of Plant Lipids", 1998, Science vol. 282, pp. 1315–1317.*
Chen et al, "Introduction and Constitutive expression of a rice chitinase gene in bread wheat using biolistic bombardment and the bar gene as a selectable marker", 1998, Theor. Appl. Genet. vol. 97 pp. 1296–1306.*

(List continued on next page.)

Primary Examiner—David T. Fox
Assistant Examiner—Anne Kubelik
(74) Attorney, Agent, or Firm—Alston & Bird LLP

(57) ABSTRACT

The invention provides isolated chitinase nucleic acids and their encoded proteins. The present invention provides methods and compositions relating to altering chitinase levels in plants. The invention further provides recombinant expression cassettes, host cells, transgenic plants, and antibody compositions.

10 Claims, No Drawings

OTHER PUBLICATIONS

Gordon–Kamm et al, "Transformation of Maize Cells and Regeneration of Fertile Transgenic Plants", 1990, The Plant Cell, vol. 2, pp. 603–618.*

Huynh, et al., 1992, *J. of Biol. Chem.*, 267(10): 6635–6640, "Antifungal Proteins from Plants Purification, Molecular Cloning, and Antifungal Properties of Chitinases from Maize Seed".

Wu, et al., 1994, *Plant Physiology*, 105(4): 1097–1105, "Molecular Analysis of Two cDNA Clones Encoding Acidic Class I Chitinase in Maize".

Iseli, et al., 1996, *FEBS Letters*, 382: 186–188, "Plant chitinases use two different hydrolytic mechanisms".

Patil and Widholm, 1997, *J. of Exper. Botany*, 48(316): 1943–1950, "Possible correlation between increased vigour and chitinase activity expression in tobacco".

Saito, et al., 1999, *Bioscience Biotechnology and Biochem.*, 63(4): 710–718, "High–multiplicity of Chitinase genes in Streptomyces coelicolor A3(2)".

Walbot, V., 1999, *EMBL Database Nucleotide and Protein Seq. AW 261292*, "Early embryo from Delaware Zea mays cDNA, mRNA sequence".

Walbot, V., 1999, *EMBL Database Nucleotide and Protein Sequences, AI667747*, "Endosperm cDNA library from Schmidt lab Zea mays cDNA, mRNA sequence".

Zhu, et al., 1993, *Plant–J. Oxford*, 3(2):203–212, "Stress induction and developmental regulatin of a rice chitinase promoter in transgenic tobacco".

Zhu, et al., 1991, *Mol. Gen. Genet.*, 226: 289–296, "Isolation and characterization of a rice gene encoding a basic chitinase".

Masoud–Sameer, et al., 1996, *Transgenic–Research*, 5(5): 313–323, "Constitutive expression of an inducible β–1, 3–glucanase in alfalfa reduces disease severity caused by the oomycete pathogen Phytophthora megasperma f. sp medicaginis, but does not reduce disease severity of chitin–containing fungi".

Zhu, et al., 1992, *Gen Pept Accession No. P25765*, "Isolation and characterization of a rice gene encoding a basic chitinase".

Huynh, et al., 1993, *GenBank Accession No. M84164*, "Antifungal proteins from plants–purification, molecular cloning and antifungal properties of chitinases from maize seed".

Huynh, et al., 1993, *GenBank Accession No. M84165*, "Antifungal proteins from plants–purification, molecular cloning and antifungal properties of chitinases from maize seed".

Wu, et al., 1995, *GenBank Accession No. L00973*, "Molecular analysis of two cDNA clones encoding acidic class I chitinase in maize".

Wu, et al., 1995, *Genbank Accession No. L16798*, "Molecular analysis of two cDNA clones encoding acidic class I chitinase in maize".

Didierjean, et al., 2000, *GenBank Accession No. S82314*, "Heavy–metal–responsive genes in maize: identification and comparison of their expression upon various forms of abiotic stress".

* cited by examiner

MAIZE CHITINASES AND THEIR USE IN ENHANCING DISEASE RESISTANCE IN CROP PLANTS

CROSS-REFERENCE TO RELATED APPLICATIONS

This application claims the benefit of U.S. Ser. No. 60/125,915 filed Mar. 24, 1999 which is herein incorporated by reference.

TECHNICAL FIELD

The present invention relates generally to plant molecular biology. More specifically, it relates to nucleic acids and methods for modulating their expression in plants.

BACKGROUND OF THE INVENTION

Disease in plants is caused by biotic and abiotic causes. Biotic causes include fungi, viruses, insects, bacteria, and nematodes. Of these, fungi are the most frequent causative agents of disease in plants. Abiotic causes of disease in plants include extremes of temperature, water, oxygen, soil pH, plus nutrient-element deficiencies and imbalances, excess heavy metals, and air pollution.

As noted, among the causative agents of infectious disease of crop plants, the phytopathogenic fungi play the dominant role. Plytopathogenic fungi cause devastating epidemics, as well as causing significant annual crop yield losses. Pathogenic fungi attack all of the approximately 300,000 species of flowering plants.

Plant disease outbreaks have resulted in catastrophic crop failures that have triggered famines and caused major social change. Generally, the best strategy for plant disease control is to use resistant cultivars selected or developed by plant breeders for this purpose. Typically, this involved elaborate breeding to incorporate natural resistance mechanisms into elite breeding material. The sources of this natural resistance were often otherwise undesirable plant materials, and so extensive backcrossing and introgression was needed to recreate the desired background with the disease resistance. Sometimes even this was not obtained, as the resistance mechanism(s) were polygenic. In short, improving disease resistance by conventional breeding is expensive in both time and money.

Increasingly various genetic engineering strategies are being put forth to create enhanced disease resistance using recombinant DNA technology and transgenic plants. Sometimes this involves isolation of a resistance gene and then discreetly inserting it into a susceptible plant by transformation. Other strategies involve engineering elevated expression of antimicrobial compounds, reactive oxygen species, which are known to be antimicrobial and/or stimulators of plant defense systems.

The potential for serious crop disease epidemics persists today, as evidenced by outbreaks of the Victoria blight of oats and southern corn leaf blight. What is needed in the art are compositions and methods for overcoming the conventional breeding method and existing genetic engineering strategies by providing discrete novel genes encoding antimicrobial/antifungal proteins. Chitinases are one such class of genes. These genes encode enzymes which hydrolyze beta-1,4-linkages in chitin, a polymer of N-acetyl-D-glucosamine. Chitin, the substrate of chitinase enzymes, is present in fungal cell walls and in the exoskeletons of insects, nematodes, and some other organisms. Consequently, chitinases have antibiotic action against such organisms, a variety of which are pathogenic on plants.

Chitinases are divided into two main groups: those of the glucosyl hydrolase family 19, which is specific to plants, and which exhibits only chitinase activity; and the glucosyl hydrolase family 18, which are chitinases, but which sometimes also have lysosyme activity. Lysozymes degrade mixed linked polymers of N-acetyl-glucosamine and N-acetyl-muramic acid. These polymers are found in bacterial cell walls. As such, those chitinases of the glucosyl hydrolase family 18 will also find utility in combating bacterial plant pathogens.

The glucosyl hydrolase family 19 is further divided into classes I, II, and IV. Class I chitinases have a signal peptide, a cysteine-rich chitin binding domain, an enzyme catalytic region, and a C-terminal extension directing the protein to the vacuole. Class II chitinases have a signal peptide and an enzyme catalytic region. Class IV chitinases have a signal peptide, an abbreviated cysteine-rich chitin binding domain, and an enzyme catalytic region. In addition, there are chitinases with minor modifications of these features.

The chitinases of glucosyl hydrolase family 18 are also known as class III chitinases. They have a signal peptide and a catalytic domain. They are structurally unrelated to the chitinases of glucosyl hydrolase family 19.

The present invention describes novel maize chitinase genes represented by cDNAs. The chitinase genes of the present invention are useful in the control of pathogens. The present invention provides these and other advantages.

SUMMARY OF THE INVENTION

In the present invention, seven chitinases of the glucosyl hydrolase family 19 are presented as partial or full-length cDNAs/proteins named: ZmCht2 (SEQ ID NO: 1/SEQ ID NO:2). ZmCht7 (SEQ ID NO:5/SEQ ID NO:6), ZmCht11 (SEQ ID NO: 11/SEQ ID NO:12), ZmCht14 (SEQ ID NO:17/SEQ ID NO:18), ZmCht15 (SEQ ID NO:19/SEQ ID NO:20), ZmCht16 (SEQ ID NO:21/SEQ ID NO:22), and ZmCht17 (SEQ ID NO:23/SEQ ID NO:24). Five chitinases of glucosyl hydrolase family 18 are presented herein as partial or full-length cDNAs/proteins and are named: ZmCht6 (SEQ ID NO:3/SEQ ID NO:4), ZmCht9 (SEQ ID NO:7/SEQ ID NO:8), ZmCht10 (SEQ ID NO:9/SEQ ID NO:10), ZmCht12 (SEQ ID NO:13/SEQ ID NO: 14), and ZmCht13 (SEQ ID NO:15/SEQ ID NO:16).

Generally, it is the object of the present invention to provide nucleic acids and proteins relating to maize chitinases. It is an object of the present invention to provide: 1) antigenic fragments of the proteins of the present invention; 2) transgenic plants comprising the nucleic acids of the present invention; 3) methods for modulating, in a transgenic plant, the expression of the nucleic acids of the present invention.

Therefore, in one aspect, the present invention relates to an isolated nucleic acid comprising a member selected from (a) a polynucleotide having a specified sequence identity to a polynucleotide of the present invention; (b) a polynucleotide which is complementary to the polynucleotide of (a); and, (c) a polynucleotide comprising a specified number of contiguous nucleotides from a polynucleotide of (a) or (b). In another aspect, the present invention relates to an isolated nucleic acid comprising a polynucleotide of specified length, which selectively hybridizes under stringent conditions to a polynucleotide of the present invention, or a complement thereof. The isolated nucleic acid can be DNA.

In another aspect, the present invention relates to recombinant expression cassettes, comprising a nucleic acid of the present invention operably linked to a promoter.

In another aspect, the present invention is directed to a host cell into which has been introduced the recombinant expression cassette.

In a further aspect, the present invention relates to an isolated protein comprising a polypeptide of the present invention and to a polypeptide of the present invention having a specified number of contiguous amino acids. Also, the present invention relates to a polypeptide having a specific sequence identity to the polypeptide of the present invention. In addition, the present invention relates to a polypeptide encoded by a polynucleotide of the present invention.

In yet another aspect, the present invention relates to a transgenic plant comprising a recombinant expression cassette comprising a plant promoter operably linked to any of the isolated nucleic acids of the present invention. The present invention also provides transgenic seed from the transgenic plant.

Finally, the present invention relates to methods of modulating the level of chitinase in a plant by a) introducing an expression cassette containing a polynucleotide of the present invention, b) culturing the plant cell under plant cell growing conditions, and c) inducing expression of the polynucleotide for a time sufficient to modulate the level of chitinase in the plant.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substances capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246: 1275–1281 (1989); and Ward, et al., *Nature* 341: 544–546 (1989); and Vaughan et al., *Nature Biotech*. 14: 309–314 (1996).

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG , which is ordinarily the only codon for tryptophan) can be modified to yield a functionally :identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of.from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17: 477–498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN AUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, reactive to a particular epitope, to bind to that epitope to a detectably greater degree (e.g., at least 2-fold over background) than the antibody binds to substantially any other epitopes in a reaction mixture comprising the particular epitope. Immunologically reactive conditions are dependent upon the format of the antibody binding reaction and typically are those utilized in immunoassay protocols. See Harlow and Lane, *Antibodies, A Laboratory Manual*, Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

Unless otherwise stated, the term "chitinase nucleic acid" is a nucleic acid of the present invention and means a nucleic acid comprising a polynucleotide of the present invention (a "chitinase polynucleotide") encoding a chitinase polypeptide. A "chitinase gene" is a gene of the present invention and refers to a heterologous genomic form of a full-length chitinase polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether nor not its origin is a plant cell. Exemplary plant promoters include, but are not limited to, those that are obtained from plants, plant viruses, and bacteria which comprise genes expressed in plant cells such Agrobacterium or Rhizobium. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "chitinase polypeptide" is a polypeptide of the present invention and refers to one or more amino acid sequences, in glycosylated or non-glycosylated form. The term is also inclusive of fragments, variants, homologs, alleles or precursors (e.g., preproproteins or proproteins) thereof. A "chitinase protein" is a protein of the present invention and comprises a chitinase polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, underexpressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all analytes lacking the epitope' which are present in the sample.

Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See Harlow and Lane, *Antibodies, A Laboratory Manual*, Cold Spring Harbor Publications, New York (1988), for a description of immunoassay formats and conditions that can be used to determine selective reactivity.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the $T_m$ can be approximated from the equation of Meinkoth and Wahl, *Anal. Biochem.*, 138:267–284 (1984): $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

GAP uses the algorithm of Needleman and Wunsch (*J Mol Biol* 48: 443–453 (1970)) to find the alignment of two complete sequences that maximizes the number of matches and minimizes the number of gaps. GAP considers all possible alignments and gap positions and creates the alignment with the largest number of matched bases and the fewest gaps. Default gap creation penalty values and gap extension penalty values in Version 10 of the Wisconsin Genetics Software Package are 8 and 2, respectively, for protein sequences. For nucleotide sequences the default gap creation penalty is 50 while the default gap extension penalty is 3. The gap creation and gap extension penalties can be expressed as an integer selected form the group of integers consisting of form 0 to 100. Thus, for example, the gap creation and gap extension penalties can be 0, 1, 2, 3, 4, 5, 6, 7, 8, 9, 10, 15, 20, 30, 40, 50, 60, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of: bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff, *Proc Natl Acad Sci USA* 89:10915).

Unless otherwise stated, sequence identity/similarity values provided herein refer to the value obtained using the BLAST 2.0 suite of programs using default parameters. Altschul et al., *Nucleic Acids Res.* 25:3389–3402 (1997) or GAP version 10 of Wisconsin Genetic Software Package using default parameters. Software for performing BLAST analyses is publicly available, e.g., through the National Center for Biotechnology Information, which has a website at the location: www.ncbi.nlm.nih.gov. This algorithm involves first identifying high scoring sequence pairs (HSPs) by identifying short words of length W in the query sequence which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0) . For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff(19989) *Proc. Natl. Acad. Sci. USA* 89: 10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5877 (1993)). One measure of similarity provided by the BLAST algorithm is the smallest sum probability (P(N)), which provides an indication of the probability that a match between two nucleotide or two amino acid sequences would occur by chance.

BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Optionally, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may.differ by conservative amino acid changes.

DETAILED DESCRIPTION OF THE INVENTION

Overview

The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues, and/or in quantities, which are uncharacteristic of non-recombinantly engineered plants. Thus, the present invention provides utility in such exemplary applications as enhancing disease resistance in plants, particularly crop plants such as maize. By "enhanced resistance" it is meant any diminishment in the disease symptoms and/or growth, viability, reproduction and dispersal of the pathogen. Without being bound by theory, this may come about by any means, including, but not limited to direct lysis of the (fungal) pathogen through weakening of the cell wall. It may also be through the release of oligochitosan elicitors that may more generally activate plant pathogen defense systems, including, but not limited to activation of resident nontransgenic chitinase gene expression, but also expression of other defense related genes and gene products.

The present invention also provides isolated nucleic acid comprising polynucleotides of sufficient length and complementarity to a gene of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms), orthologs, or paralogs of the gene, or for site directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme, or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, for identification of homologous polypeptides from other species, or for purification of polypeptides of the present invention.

The isolated nucleic acids and polypeptides of the present invention can be used over a broad range of plant types, particularly monocots such as the species of the family Gramineae including Hordeum, Secale, Triticum, Sorghum (e.g., S. bicolor), Oryza, Avena, and Zea (e.g., Z. mays). The isolated nucleic acid and proteins of the present invention can also be used in species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum,: Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, and Lolium.

Pathogens of the invention include, but are not limited to, viruses or viroids, bacteria, insects, fungi, and the like. Specific fungal pathogens for the major crops include: Soybeans: *Phytophthora megasperma* fsp. glycinea, *Macrophomina phaseolina, Rhizoctonia solani, Sclerotinia sclerotiorum, Fusarium oxysporum, Diaporthe phaseolorum* var. sojae (*Phomopsis sojae*), *Diaporthe phaseolorum* var. caulivora, *Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. glycinea, *Xanthomonas campestris* p.v. phaseoli, *Microsphaera diffusa, Fusarium semitectum, Phialophora gregata*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. insidiosum, *Pythium ultimum, Pythium irregulare, Pythium splendens, Pythium debaryanum, Pythium aphanidermatum, Phytophthora megasperma, Peronospora trifoliorum, Phoma medicaginis* var. medicaginis, *Cercospora medicaginis, Pseudopeziza medicaginis, Leptotrochila medicaginis, Fusar-atrum, Xanthomonas campestris* p.v. alfalfae, *Aphanomyces euteiches, Stemphylium herbarum, Stemphylium alfalfae*; Wheat: *Pseudomonas syringae* p.v. atrofaciens, *Urocystis agropyri, Xanthomonas campestris* p.v. translucens, *Pseudomonas syringae* p.v. syringae, *Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. tritici, *Puccinia graminis* f.sp. tritici, *Puccinia recondita* f.sp. tritici, *Puccinia striiformis, Pyrenophora triticirepentis, Septoria nodorum, Septoria tritici, Septoria avenae, Pseudocercosporella herpotrichoides, Rhizoctonia solani, Rhizoctonia cerealis, Gaeumannomyces graminis* var. tritici, *Pythium aphanidermatum, Pythium arrhenomanes, Pythium ultimum, Bipolaris sorokiniana*; Sunflower: *Plasmophora halstedii, Sclerotinia sclerotiorum, Aster Yellows, Septoria helianthi, Phomopsis helianthi, Alternaria helianthi, Alternaria zinniae, Botrytis cinerea,*

*Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. Carotovora, *Cephalosporium acremonium, Phytophthora cryptogea, Albugo tragopogonis;* Maize: *Fusarium moniliforme* var. subglutinans, *Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis,* Kabatiemaydis, *Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganese* subsp. nebraskense, *Trichoderma viride, Claviceps sorghi, Pseudonomas avenae, Erwinia chrysanthemi* p.v. Zea, *Erwinia corotovora, Cornstunt spiroplasma, Diplodia macrospora, Sclerophthora macrospora, Peronosclerospora sorghi, Peronosclerospora philippinesis, Peronosclerospora maydis, Peronosclerospora sacchari, Spacelotheca reiliana, Physopella zea, Cephalosporium maydis, Caphalosporium acremonium*; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. syringae, *Xanthomonas campestris* p.v. holcicola *Pseudomonas andropogonis, Puccinia purpurea, Macrophomina phaseolina, Perconia circinata, Fusarium moniliforme, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi, Claviceps sorghi, Rhizoctonia solani, Acremonium strictum, Sclerophthona macrospora, Peronosclerospora sorghi, Peronosclerospora philippinensis, Scierospora graminicola, Fusarium graminearum, Fusarium oxysporum, Pythium arrhenomanes, Pythium graminicola,* etc.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:

(a) a polynucleotide encoding a polypeptide of SEQ ID NOS: 2, 4, 6, 8, 10, 12, 14, 16, 18, 20, 22, 24, 26, 28, and 30, and conservatively modified and polymorphic variants thereof, including exemplary polynucleotides of SEQ ID NOS: 1, 3, 5, 7, 9, 11, 13, 15, 17, 19, 21, 23, 25, 27, 29, and 31;

(b) a polynucleotide which is the product of amplification from a *Zea mays* nucleic acid library using primer pairs which selectively hybridize under stringent conditions to loci within a polynucleotide selected from the group consisting of SEQ ID NOS: 1, 3, 5, 7, 9, 11, 13, 15, 17, 19, 21, 23, 25, 27, 29, and 31, wherein the polynucleotide has substantial sequence identity to a polynucleotide selected from the group consisting of SEQ ID NOS: 1, 3, 5, 7, 9, 11, 13, 15, 17, 19, 21, 23, 25, 27, 29, and 31;

(c) a polynucleotide which selectively hybridizes to a polynucleotide of (a) or (b);

(d) a polynucleotide having a specified sequence identity with polynucleotides of (a), (b), or (c);

(e) complementary sequences of polynucleotides of (a), (b), (c), or (d); and (f) a polynucleotide comprising at least a specific number of contiguous nucleotides from a polynucleotide of (a), (b), (c), (d), or (e).

A. Polynucleotides Encoding A Polypeptide of the Present Invention or Conservatively Modified or Polymorphic Variants Thereof The present invention provides isolated nucleic acids comprising a polynucleotide of the present invention, wherein the polynucleotide encodes a polypeptide of the present invention, or conservatively modified or polymorphic variants thereof. Accordingly, the present invention includes polynucleotides of SEQ ID NOS: 1, 3, 5, 7, 9, 11, 13, 15, 17, 19., 21, 23, 25, 27, 29, and 31, and silent variations of polynucleotides encoding a polypeptide of SEQ ID NOS: 2, 4, 6, 8, 10, 12, 14, 16, 18, 20, 22, 24, 26, 28, and 30. The present invention further provides isolated nucleic acids comprising polynucleotides encoding conservatively modified variants of a polypeptide of SEQ ID NOS: 2, 4, 6, 8, 10, 12, 14, 16, 18, 20, 22, 24, 26, 28, and 30. Conservatively modified variants can be used to generate or select antibodies immunoreactive to the non-variant polypeptide. Additionally, the present invention further provides isolated nucleic acids comprising polynucleotides encoding one or more allelic (polymorphic) variants of polypeptides/polynucleotides. Polymorphic variants are frequently used to follow segregation of chromosomal regions in, for example, marker assisted selection methods for crop improvement.

B. Polynucleotides Amplified from a *Zea mays* Nucleic Acid Library

The present invention provides an isolated nucleic acid comprising a polynucleotide of the present invention, wherein the polynucleotides are amplified from a *Zea mays* nucleic acid library. *Zea mays* lines B73, A632, BMS, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using a full-length cDNA synthesis method. Examples of such methods include Oligo-Capping (Maruyama, K. and Sugano, S. *Gene* 138: 171–174, 1994), Biotinylated CAP Trapper (Carninci, P., Kvan, C., et al. *Genomics* 37: 327–336, 1996), and CAP Retention Procedure (Edery, E., Chu, L. L., et al. *Molecular and Cellular Biology* 15: 3363–3371, 1995). cDNA synthesis is often catalyzed at 50–55° C. to prevent formation of RNA secondary structure. Examples of reverse transcriptases that are relatively stable at these temperatures are SuperScript II Reverse Transcriptase (Life Technologies, Inc.), AMV Reverse Transcriptase (Boehringer Mannheim) and RetroAmp Reverse Transcriptase (Epicentre). Rapidly growing tissues, or rapidly dividing cells are preferably used as mRNA sources.

The present invention also provides subsequences of the polynucleotides of the present invention. A variety of subsequences can be obtained using primers which selectively hybridize under stringent conditions to at least two sites within a polynucleotide of the present invention, or to two sites within the nucleic acid which flank and comprise a polynucleotide of the present invention, or to a site within a polynucleotide of the present invention and a site within the nucleic acid which comprises it. Primers are chosen to selectively hybridize, under stringent hybridization conditions, to a polynucleotide of the present invention. Generally, the primers are complementary to a subsequence of the target nucleic acid which they amplify. As those skilled in the art will appreciate, the sites to which the primer pairs will selectively hybridize are chosen such that a single contiguous nucleic acid can be formed under the desired amplification conditions.

In optional embodiments, the primers will be constructed so that they selectively hybridize under stringent conditions to a sequence (or its complement) within the target nucleic acid which comprises the codon encoding the carboxy or amino terminal amino acid residue (i.e., the 3' terminal coding region and 5' terminal coding region, respectively) of the polynucleotides of the present invention. Optionally within these embodiments, the primers will be constructed to selectively hybridize entirely within the coding region of the target polynucleotide of the present invention such that the product of amplification of a cDNA target will consist of the coding region of that cDNA. The primer length in nucleotides is selected from the group of integers consisting of from at least 15 to 50. Thus, the primers can be at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides in length. Those of skill will recognize that a lengthened primer sequence can be employed to increase specificity of binding (i.e., annealing) to a target sequence. A non-annealing sequence at the 5'end of a primer (a "tail") can be added, for example, to introduce a cloning site at the terminal ends of the amplicon.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc, Catalog '97, p.354.

Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and *Current Protocols in Molecular Biology*, Unit 15.6, Ausubel, et al., Eds, Greene Publishing and Wiley-Interscience, New York (1995); Frohman and Martin, *Techniques* 1:165 (1989).

C. Polynucleotides Which Selectively Hybridize to a Polynucleotide of (A) or (B)

The present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: corn, canola, soybean, cotton, wheat, sorghum, sunflower, oats, sugar cane, millet, barley, and rice. Optionally, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having a Specific Sequence Identity with the Polynucleotides of (A), (B) or (C)

The present invention provides isolated nucleic acids comprising polynucleotides of the present invention, wherein the polynucleotides have a specified identity at the nucleotide level to a polynucleotide as disclosed above in sections (A), (B), or (C), above. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90%, or 95%.

E. Polynucleotides Complementary to the Polynucleotides of (A)–(D)

The present invention provides isolated nucleic acids comprising polynucleotides complementary to the polynucleotides of paragraphs A–E, above. As those of skill in the art will recognize, complementary sequences base-pair throughout the entirety of their length with the polynucleotides of sections (A)–(D) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

F. Polynucleotides Which are Subsequences of the Polynucleotides of (A)–(E)

The present invention provides isolated nucleic acids comprising polynucleotides which comprise at least 15 contiguous bases from the polynucleotides of sections (A) through (E) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90 95, 100, 110, 120, 130, 140, 150, 160, 170, 180, 190, 200, 250, 300, 350, 400, 450, 500, 600, 700, 800, 900 or 1000 contiguous nucleotides in length from the polynucleotides of (A)–(E). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, 200, 300, 400, 500, 600, 700, 800, 900, or 1000 nucleotides.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one linear epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates. Subsequences may also be used in antisense technology to suppress expression of a protein.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is Zea mays.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. While isolation of RNA, and construction of cDNA and genomic libraries is well known to those of ordinary skill in the art, the following highlights some of the methods employed.

A1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of organelles and proteins, followed by precipitation of nucleic acids. Extraction of total RNA from plant cells can be accomplished by a variety of means. Frequently, extraction buffers include a strong detergent such as SDS and an organic denaturant such as guanidinium isothiocyanate, guanidine hydrochloride or phenol. Following total RNA isolation, poly(A)$^+$ mRNA is typically purified from the remainder RNA using oligo(dT) cellulose. Exemplary total RNA and mRNA isolation protocols are described in Plant Molecular Biology: A Laboratory Manual, Clark, Ed., Springer-Verlag, Berlin (1997); and, Current Protocols in Molecular Biology, Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli Inc., PA). See also, U.S. Pat. Nos. 5,614,391; and, 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a cDNA library generally entails five steps. First, first strand cDNA synthesis is initiated from a poly(A)$^+$ mRNA template using a poly(dT) primer or random hexanucleotides. Second, the resultant RNA-DNA hybrid is converted into double stranded cDNA, typically by reaction with a combination of RNAse H and DNA polymerase I (or Klenow fragment). Third, the termini of the double stranded cDNA are ligated to adaptors. Ligation of the adaptors can produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: Plant Molecular Biology: A Laboratory Manual, Clark, Ed., Springer-Verlag, Berlin (1997); and, Current Protocols in Molecular Biology, Ausubel, et al., Eds., Greene Publishing and Wiley-Interscience, New York (1995). cDNA synthesis kits are available from a variety of commercial vendors such as Stratagene or Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene's lambda ZAP Express (cDNA cloning vector with 0 to 12 kb cloning capacity).

An exemplary method of constructing a greater than 95% pure full-length cDNA library is described by Carninci et al., Genomics, 37:327–336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al., *Mol. Cell Biol.*,15(6):3363–3371 (1995); and, PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, *Nucl. Acids. Res.*, 18(19):5705–5711 (1990); Patanjali et al., *Proc. Natl. Acad. U.S.A.*, 88:1943–1947 (1991); U.S. Pat. Nos. 5,482,685, and 5,637,685. In an exemplary method described by Soares et al., normalization resulted in reduction of the abundance of clones from a range of four orders of magnitude to a narrow range of only 1 order of magnitude. *Proc. Natl. Acad. Sci.* USA, 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.*, 16(22):10937 (1988); *Current Protocols in Molecular Biology*, Ausubel, et al., Eds., Greene Publishing and Wiley-Interscience, New York (1995); and, Swaroop et al., *Nucl. Acids Res.*, 19)8):1954 (1991). cDNA subtraction kits are commercially available. See, e.g., PCR-Select (Clontech, Palo Alto, Calif.).

A4. Construction of a Genomic Library

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques*, 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.*, 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polypeptide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A number of promoters can be used in the practice of the invention. A plant promoter fragment can be employed which will direct expression of a polynucleotide of the present invention in all tissues of a regenerated plant. Such promoters are referred to herein as "constitutive" promoters and are active under most environmental conditions and stated of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter (Christensen, et al. *Plant Mol Biol* 18, 675–689 (1992); Bruce, et al., *Proc Natl Acad Sci USA* 86, 9692–9696 (1989)), the Smas promoter, the cinnamyl alcohol dehydrogenase promoter (U.S. Pat. No. 5,683,439), the Nos promoter, the pEmu promoter, the rubisco promoter, the GRP1-8 promoter, the maize constitutive promoters described in PCT Publication No. WO 99/43797 which include the histone H2B, metallothionein, alpha-tubulin 3, elongation factor efla, ribosomal protein rps8, chlorophyll a/b binding protein, and glyceraldehyde-3-phosphate dehydrogenase. promoters, and other transcription initiation regions from various plant genes known to those of skill. Particularly preferred is the maize ubiquitin 1 promoter.

Where a promoter is expressed at unacceptably high levels, portions of the promoter sequence can be deleted or modified to decrease expression levels. Additionally, to obtain a varied series in the level of expression, one can also make a set of transgenic plants containing the polynucleotides of the present invention with a strong constitutive promoter, and then rank the transgenic plants according to the observed level of expression. The transgenic plants will show a variety in performance, from high expression to low expression. Factors such as chromosomal position effect, cosuppression, and the like will affect the expression of the polynucleotide.

Alternatively, the plant promoter can direct expression of a polynucleotide of the present invention under environmental control. Such promoters are referred to here as "inducible" promoters. Environmental conditions that may effect transcription by inducible promoters include pathogen attack, anaerobic conditions, or the presence of light. Examples of inducible promoters are the Adhl promoter, which is inducible by hypoxia or cold stress, the Hsp70 promoter, which is inducible by heat stress, and the PPDK promoter, which is inducible by light. Examples of pathogen-inducible promoters include those from proteins, which are induced following infection by a pathogen; e.g., PR proteins, SAR proteins, beta-1,3-glucanase, chitinase, etc. See, for example, Redolfi, et al., *Meth J. Plant Pathol.* 89:245–254 (1983); Uknes et al., *The Plant Cell* 4:645–656 (1992); Van Loon, *Plant Mol. Virol.* 4:111–116 (1985); PCT Publication No. WO 99/43819.

Of interest are promoters that are expressed locally at or near the site of pathogen infection. See, for example, Marineau, et al., *Plant Mol Biol* 9:335–342 (1987); Matton, et al., *Molecular Plant-Microbe Interactions* 2:325–342 (1987); Somssich et al., *Proc Natl Acad Sci USA* 83:2427–2430 (1986); Somssich et al., *Mole Gen Genetics* 2:93–98 (1988); Yang, *Proc Natl Acad Sci USA* 93:14972–14977. See also, Chen, et al., *Plant J* 10:955–966 (1996); Zhang and Sing, *Proc Natl Acad Sci USA* 91:2507–2511 (1994); Warner, et al., *Plant J* 3:191–201 (1993), and Siebertz, et al., *Plant Cell* 1:961–968 (1989), all of which are herein incorporated by reference. Of particular interest is the inducible promoter for the maize PRms gene, whose expression is induced by the pathogen *Fusarium moniliforme* (see, for example, Cordero, et al., *Physiol Molec Plant Path* 41:189–200 (1992) and is herein incorporated by reference.

Additionally, as pathogens find entry into plants through wounds or insect damage, a wound inducible promoter may be used in the constructs of the invention. Such wound inducible promoter include potato proteinase inhibitor (pin II) gene (Ryan, *Annu Rev Phytopath* 28:425–449 (1990); Duan, et al., *Nat Biotech* 14:494–498 (1996)); wun1 and wun 2, U.S. Pat. No. 5,428,148; win1 and win2 (Stanford et al., *Mol Gen Genet* 215:200–208 (1989)); systemin (McGurl, et al., *Science* 225:1570–1573 (1992)); WIP1 (Rohmeier, et al., *Plant Mol Biol* 22:783–792 (1993); Eckelkamp, et al., *FEB Letters* 323:73–76 (1993)); MPI gene (Cordero, et al., *The Plant J* 6(2): 141–150(1994)); and the like, herein incorporated by reference.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. An exemplary promoter for leaf- and stalk-preferred expression is MS8-15 (WO 98/00533). Examples of seed-preferred promoters included, but are not limited to, 27 kD gamma zein promoter and waxy promoter (Boronat, et al., *Plant Sci*, 47:95–102 (1986); Reina, et al., *Nucleic Acids Res* 18(21):6426 (1990); and Kloesgen, et al., *Mol Gen Genet* 203:237–244 (1986)). Promoters that express in the embryo, pericarp, and endosperm are disclosed in U.S. applications Ser. No. 60/097,233 filed Aug. 20, 1998 and U.S. applications Ser. No. 60/098,230 filed Aug. 28, 1998 both of which are hereby incorporated by reference. The operation of a promoter may also vary depending on its location in the genome. Thus, a developmentally regulated promoter may become fully or partially constitutive in certain locations. A developmentally regulated promoter can also be modified, if necessary, for weak expression.

Both heterologous and non-heterologous (i.e. endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold, Buchman and Berg, *Mol. Cell biol.* 8: 4395–4405 (1988); Callis et al., *Genes Dev.* 1: 1183–1200(1987). Such intron enhancement of gene expression is typically greatest when placed near the 5' end of the transcription unit. Use of the maize introns Adh1-S intron 1, 2, and 6, the Bronze-1 intron are known in the art. See generally, *The Maize Handbook*, Chapter 116, Freeling and Walbot, Eds., Springer, New York (1994).

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-induced (Ti) plasmid of *Agrobacterium tumefaciens* described by Rogers et al., *Meth. In Enzymol.*, 153:253–277 (1987). These vectors are plant integrating vectors in that upon transformation, the vectors integrate a portion of vector DNA into the genome of the host plant. Exemplary *A. tumefaciens* vectors useful herein are plasmids pKYLX6 and pKYLX7 of Schardl et al., *Gene*, 61:1–11(1987) and Berger et al., *Proc. Natl. Acad. Sci. U.S.A.*, 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci* (*USA*) 85:8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2:279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334:585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA meditated by incorporation of a modified nucleotide which was capable of activating cleavage (*J Am Chem Soc* (1987) 109:1241–1243). Meyer, R. B. et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides meditated by psoralen was disclosed by Lee, B. L., et al., *Biochemistry* (1988) 27:3197–3203. Use of crosslinking in triple-helix forming probes was also disclosed by Home et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and 5,681,941.

Proteins

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

As those of skill will appreciate, the present invention includes catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present: invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus sp.* and Salmonella (Palva, et al., *Gene* 22: 229–235 (1983); Mosbach, et al., *Nature* 302: 543–545 (1983)).

B. Expression in Eukaryotes

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Two widely utilized yeast for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., Immunol. Rev. 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See, Schneider, *J. Embryol. Exp. Morphol.* 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in DNA Cloning Vol. II a *Practical Approach*, D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for effective transformation/transfection may be employed.

A. Plant Transformation

The genes of the present invention can be used to transform any plant. In this manner, genetically modified plants, plant cells, plant tissue, seed, and the like can be obtained. Transformation protocols may vary depending on the type of plant cell, i.e. monocot or dicot, targeted for transformation. Suitable methods of transforming plant cells include microinjection (Crossway et al., (1986) *BioTechniques* 4:320–334), electroporation (Riggs et al. (1986) *Proc. Natl. Acad. Sci. USA* 83:5602–5606, Agrobacterium mediated transformation (Hinchee et al., (1988) *Biotechnology* 6:915–921), direct gene transfer (Paszkowski et al., (1984) *EMBO J.* 3:2717–2722), and ballistic particle acceleration (see, for example, Sanford et al., U.S. Pat. No. 4,945,050; Tomes et al., "Direct DNA Transfer into Intact Plant Cells via Microprojectile Bombardment" In Gamborg and Phillips (Eds.) *Plant Cell, Tissue and Organ Culture: Fundamental Methods*, Springer-Verlag, Berlin (1995); and McCabe et al., (1988) *Biotechnology* 6:923–926). Also see, Weissinger et al., (1988) *Annual Rev. Genet.* 22:421–477; Sanford et al., (1987) *Particulate Science and Technology* 5:27–37 (onion); Christou et al., (1988) *Plant Physiol.* 87:671–674 (soybean); McCabe et al., (1988) *Bio/Technology* 6:923–926 (soybean); Datta et al., (1990) *Biotechnology* 8:736–740 (rice); Klein et al., (1988) *Proc. Natl. Acad. Sci. USA* 85:4305–4309 (maize); Klein et al., (1988) *Biotechnology* 6:559–563 (maize); Tomes et al., "Direct DNA Transfer into Intact Plant Cells via Microprojectile Bombardment" in Gamborg and Phillips (Eds.) *Plant Cell, Tissue and Organ Culture: Fundamental Methods*, Springer-Verlag, Berlin (1995) (maize); Klein et al., (1988) *Plant Physiol.* 91:440–444 (maize) Fromm et al., (1990)*Biotechnology* 8:833–839 (maize); Hooydaas-Van Slogteren & Hooykaas (1984) *Nature* (*London*) 311:763–764; Bytebier et al., (1987) *Proc. Natl. Acad. Sci. USA* 84:5345–5349 (Liliaceae); De Wet et al., (1985) In *The Experimental Manipulation of Ovule Tissues* ed. G. P. Chapman et al., pp. 197–209. Longman, N.Y. (pollen); Kaeppler et al., (1990) *Plant Cell Reports* 9:415–418; and Kaeppler et al., (1992) *Theor. Appl. Genet.*

84:560–566 (whisker-meditated transformation); D'Halluin et al., (1992) *Plant Cell* 4:1495–1505 (electroporation); LI et al., (1993) *Plant Cell Reports* 12:250–255 and Christou and Ford (1995) *Annals of Botany* 75:745–750 (maize via *Agrobacterium tumefaciens*); all of which are herein incorporated by reference.

The cells, which have been transformed, may be grown into plants in accordance with conventional ways. See, for example, McCormick et al. (1986) *Plant Cell Reports*, 5:81–84. These plants may then be grown, and either pollinated with the same transformed strain or different strains, and the resulting hybrid having the desired phenotypic characteristic identified. Two or more generations may be grown to ensure that the subject phenotypic characteristics is stable maintained and inherited and then seeds harvested to ensure the desired phenotype or other property has been achieved. One of skill will recognize that after the recombinant expression cassette is stably incorporated in transgenic plants and confirmed to be operable, it can be introduced into other plants by sexual crossing. Any of number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plans that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts compromise the introduced nucleic acid sequences.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Backcrossing to a parental plant and out-crossing with a non-transgenic plant are also contemplated.

B. Transfection of Prokaryotes, Lower Eukaryotes, and Animal Cells

Animal and lower eukaryotic (e.g., yeast) host cells are competent or rendered competent for. transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol. 2: Special Methods in Peptide Synthesis, Part A.;* Merrifield, et al., *J. Am. Chem. Soc.* 85: 2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation. Expressed protein may also be detected using chitinase enzyme activity assays using various sources of chitinase substrates.

Modulating Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the ratio of the polypeptides of the present invention in a plant. The method comprises introducing into a plant cell with a recombinant expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or the ratios of the polypeptides in the plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or ratios of polypeptides of the present invention in the plant. Plant forming conditions are well known in the art and discussed briefly, supra.

In general, concentration or the ratios of the polypeptides is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal: segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, *The DNA Revolution* by Andrew H. Paterson 1996 (Chapter 2) in: *Genome Mapping in Plants* (ed. Andrew H. Paterson) by Academic Press/R. G. Landis Company, Austin, Tex., pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or I cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or restriction-enzyme treated (e.g., Pst I) genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific ligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res*. 15:8125 (1987)) and the 7-methylguanosine cap structure (Drummond et al., *Nucleic Acids Res*. 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell, Biol*. 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res*. 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be fill-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 96/19256. See also, Zhang, J.-H., et al. *Proc. Natl. Acad. Sci. USA* 94:4504–4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140%.or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide, sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phylums, or kingdoms. For example, a polynucleotide having a consensus sequences from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum' probability (P(N)). Various suppliers of sequence-analysis software are listed in chapter 7 of *Current Protocols in Molecular Biology*, F. M. Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0. 1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Assays for Compounds that Modulate Enzymatic Activity or Expression

The present invention also provides means for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Generally, the polypeptide will be present in a range sufficient to determine the effect of the compound, typically about 1 nM to 10 µM. Likewise, the compound will be present in a concentration of from about 1 µM to 10 µM. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics is well known in the art. See, e.g., Segel, *Biochemical Calculations*, $2^{nd}$ ed., John Wiley and Sons, New York (1976).

Although the present invention has been described in some detail by way of illustration and example for purposes of clarity of understanding, it will be obvious that certain changes and modifications may be practiced within the scope of the appended claims.

EXAMPLE 1

This example describes the construction of the cDNA libraries.

Total RNA Isolation

Total RNA was isolated from corn tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal. Biochem.* 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+RNA Isolation

The selection of poly(A)+RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringency conditions and eluted by RNase-free deionized water.

In preferred embodiments, the mRNA for the following maize polynucleotides is isolated from the following tissues:

SEQ ID NO:1 (ZmCht-2) is obtained from callus 5 days after treatment with auxin ($10^{-5}$ M–$10^{-6}$ M) ceases, from variety B73.

SEQ ID NO:3 (ZmCht-6) is obtained from roots from the V5 stage of variety B73.

SEQ ID NO:5 (ZmCht-7) is obtained from shoots of variety PHRE1 (U.S. Pat. No. 5,416,254).

SEQ ID NO:7 (ZmCht-9) is obtained from cell suspensions of variety Black Mexican Sweet (BMS).

SEQ ID NO:9 (ZmCht-10) is obtained from shoots of variety PHRE1 (U.S. Pat. No. 5,416,254).

SEQ ID NO:11 (ZmCht-11) is obtained from ear shoots of V12 stage B73.

SEQ ID NO:13 (ZmCht-12) is obtained from B73 embryos one day after imbibition.

SEQ ID NO:15 (ZmCht-13) is obtained from roots from B73 seedlings.

SEQ ID NO:17 (ZmCht-14) is obtained from B73 leaves infected with *Cochliobolus heterostrophus*.

SEQ ID NO:19 (ZmCht-15) is obtained from B73 leaves infected with *Cochliobolus heterostrophus*.

SEQ ID NO:21 (ZmCht-16) is obtained from leaves of the les9 mutant (Maize Genetic Cooperative Stock Center, University of Illinois, Urbana, Ill.).

SEQ ID NO:23 (ZmCht-17) is obtained from B73 stem whorls infected with European corn borer (ECB).

SEQ ID NO:25 (ZmCht-18) is obtained from shoots of variety PHRE1 (U.S. Pat. No. 5,416,254).

SEQ ID NO:27 (ZmCht-19) is obtained from log phase suspension cells of BMS.

SEQ ID NO:29 (ZmCht-20) is obtained from premeiotic ear shoots of variety B73.

cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

EXAMPLE 2

This example describes cDNA sequencing and library subtraction.

Sequencing Template Preparation

Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure were plated out on 22×22 $cm^2$ agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 $cm^2$ nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper: prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook,J., Fritsch, E. F. and Maniatis, T., (in Molecular Cloning: A laboratory Manual, $2^{nd}$ Edition). The following probes were used in colony hybridization:

1. First strand cDNA from the same tissue as the library was made from to remove the most redundant clones.

2. 48–192 most redundant cDNA clones from the same library based on previous sequencing data.
3. 192 most redundant cDNA clones in the entire corn sequence database.
4. A Sal-A20 oligo nucleotide: TCG ACC CAC GCG TCC GAA AAA AAA AAA AAA AAA AAA (SEQ ID NO:32), removes clones containing a poly A tail but no cDNA.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

EXAMPLE 3

This example describes identification of the gene from a computer homology search.

Gene identities were determined by conducting BLAST (Basic Local Alignment Search Tool; Altschul, S. F., et al., (1993) *J. Mol. Biol.* 215:403–410; see also www.ncbi.nlm.nih.gov/BLAST/) searches under default parameters for similarity to sequences contained in the BLAST "nr" database (comprising all non-redundant Gen-Bank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. *Nature Genetics* 3:266–272 (1993)) provided by the NCBI. In some cases, the sequencing data from two or more clones containing overlapping segments of DNA were used to construct contiguous DNA sequences.

A search of Derwent's (United Kingdom, London) GeneSeq database with the chitinase clones revealed no maize chitinase that are exact or even close. The closest hit was a rice RCH10 clone (accessions Q31408 and Q81346) that is a class I chitinase. Five maize chitinases have been published. They are arbitrarily named here as ZmCht1 (accession M84164), ZmCht2 (accession M84165), ZmCht3 (accession L00973), ZmCht4 (accession L16798) and ZmCth5 (accession S82314).

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed is:

1. An isolated nucleic acid encoding a polypeptide having chitinase enzyme activity, said nucleic acid comprising a member selected from the group consisting of:
   (a) the polynucleotide sequence set forth in SEQ ID NO:9; and
   (b) a polynucleotide which is complementary to the polynucleotide of (a).

2. A recombinant expression cassette comprising the nucleic acid of claim 1 operably linked, in sense or antisense orientation, to a promoter.

3. A host cell comprising the recombinant expression cassette of claim 2.

4. A transgenic plant comprising the recombinant expression cassette of claim 2.

5. The transgenic plant of claim 4, wherein said plant is a monocot.

6. The transgenic plant of claim 4, wherein said plant is selected from the group consisting of corn, soybean, sunflower, sorghum, canola, wheat, alfalfa, cotton, rice, barley, and millet.

7. A stably transformed transgenic seed from the transgenic plant of claim 4, wherein the seed comprises the recombinant expression cassette.

8. A method of modulating the level of chitinase in a plant, comprising:
   (a) introducing into a plant cell a recombinant expression cassette comprising the nucleic acid of claim 1 operably linked to a promoter;
   (b) culturing the plant cell under plant cell growing conditions;
   (c) regenerating a plant from said plant cell; and
   (d) inducing expression of said polypeptide for a time sufficient to modulate the level of chitinase in said plant.

9. The method of claim 8, wherein the plant is maize.

10. An isolated nucleic acid encoding a polypeptide having chitinase enzyme activity, said nucleic acid comprising a member selected from the group consisting of:
   (a) a polynucleotide sequence that encodes a polypeptide comprising the amino acid sequence set forth in SEQ ID NO:10; and
   (b) a polynucleotide which is complementary to the polynucleotide of (a).

* * * * *

SEQUENCE LISTING

```
<160> NUMBER OF SEQ ID NOS: 32

<210> SEQ ID NO 1
<211> LENGTH: 1094
<212> TYPE: DNA
<213> ORGANISM: Zea mays
<220> FEATURE:
<221> NAME/KEY: CDS
<222> LOCATION: (51)...(893)

<400> SEQUENCE: 1
cggacgcgtg ggtttgtcag aagctcaaat actgatctca ctgatccagt atg gct         56
                                                        Met Ala
                                                         1 atg gca aag gca ggc gcg ccg agg gtc tcg gcg gcc cag ctg gtg act       104
Met Ala Lys Ala Gly Ala Pro Arg Val Ser Ala Ala Gln Leu Val Thr
        5                   10                  15 ctc ggg cta tca ctc ctc tgc gct gtc gcc ggc ccg gcc gcc gcg cag       152
Leu Gly Leu Ser Leu Leu Cys Ala Val Ala Gly Pro Ala Ala Ala Gln
    20                  25                  30 aac tgc ggc tgc cag cca aac gta tgc tgc agc aag ttt ggc tac tgc       200
Asn Cys Gly Cys Gln Pro Asn Val Cys Cys Ser Lys Phe Gly Tyr Cys
35                  40                  45                  50 ggc acg acc gac gag tac tgc ggc gac ggg tgc cag tcg ggc ccg tgc       248
Gly Thr Thr Asp Glu Tyr Cys Gly Asp Gly Cys Gln Ser Gly Pro Cys
                55                  60                  65 cgc tcg ggc ggc ggc ggc agc agt ggc ggc ggt ggt gcg aac gtg gct       296
Arg Ser Gly Gly Gly Gly Ser Ser Gly Gly Gly Gly Ala Asn Val Ala
            70                  75                  80 agc gtc gtc acc ggc tcc ttc ttc aac ggc atc aag agc cag gcc ggg       344
Ser Val Val Thr Gly Ser Phe Phe Asn Gly Ile Lys Ser Gln Ala Gly
        85                  90                  95
```

```
agc ggg tgc gag ggc aag aac ttc tac acc cgg agc gcg ttc ctg agc   392
Ser Gly Cys Glu Gly Lys Asn Phe Tyr Thr Arg Ser Ala Phe Leu Ser
        100                 105                 110 gcc gtc aag gcg tac cca ggc ttc gcc cat ggc ggg tcg cag gtg cag   440
Ala Val Lys Ala Tyr Pro Gly Phe Ala His Gly Gly Ser Gln Val Gln
115                 120                 125                 130 ggc aag cgc gag atc gcc gcc ttc ttc gcg cac gcc acg cac gag acc   488
Gly Lys Arg Glu Ile Ala Ala Phe Phe Ala His Ala Thr His Glu Thr
                135                 140                 145 ggg cat ttc tgc tac atc agc gag atc aac aag agc aac gcc tac tgc   536
Gly His Phe Cys Tyr Ile Ser Glu Ile Asn Lys Ser Asn Ala Tyr Cys
            150                 155                 160 gac ccg acc aag agg cag tgg ccg tgc gcc gcg ggg cag aag tac tac   584
Asp Pro Thr Lys Arg Gln Trp Pro Cys Ala Ala Gly Gln Lys Tyr Tyr
        165                 170                 175 ggg cgc ggc ccg ctg cag atc tcg tgg aac tac aac tac ggg ccc gcg   632
Gly Arg Gly Pro Leu Gln Ile Ser Trp Asn Tyr Asn Tyr Gly Pro Ala
    180                 185                 190 ggg agg gcc atc ggc ttc gac ggg ctc ggg gac ccc ggc agg gtg gcg   680
Gly Arg Ala Ile Gly Phe Asp Gly Leu Gly Asp Pro Gly Arg Val Ala
195                 200                 205                 210 cgg gac gcc gtg gtg gcg ttc aag gcg gcg ctc tgg ttc tgg atg aac   728
Arg Asp Ala Val Val Ala Phe Lys Ala Ala Leu Trp Phe Trp Met Asn
                215                 220                 225 agc gtg cac ggg gtg gtg ccg cag ggg ttc ggc gcc acc acc agg gcc   776
Ser Val His Gly Val Val Pro Gln Gly Phe Gly Ala Thr Thr Arg Ala
            230                 235                 240 atc aac ggc gcc ctc gag tgc ggc ggg aac aac ccc gcc cag atg aac   824
Ile Asn Gly Ala Leu Glu Cys Gly Gly Asn Asn Pro Ala Gln Met Asn
        245                 250                 255 gcg cgc gtc ggc tac tac agg cag tac tgc cgc cag ctc ggc gtc gac   872
Ala Arg Val Gly Tyr Tyr Arg Gln Tyr Cys Arg Gln Leu Gly Val Asp
    260                 265                 270 ccc ggg ccc aac ctc acc tgc taggctaggc ggcatcggcg gacggcgggg      923
Pro Gly Pro Asn Leu Thr Cys
275                 280 gccttcaggc cttgtgctcg gcgtcgcatc gcaccctcgc gcgcgaaacc gagcaatagt  983
gacaataaaa cgccggggct agctgagcct gtttgttcga cttcgacctg aataatgaag 1043 cagctgtgtt aaaaaaaaaa aaaaaaaaaa aaaaaaaaaa aaaaaaaaaa a          1094

<210> SEQ ID NO 2
<211> LENGTH: 281
<212> TYPE: PRT
<213> ORGANISM: Zea mays

<400> SEQUENCE: 2

Met Ala Met Ala Lys Ala Gly Ala Pro Arg Val Ser Ala Ala Gln Leu
 1               5                  10                  15

Val Thr Leu Gly Leu Ser Leu Leu Cys Ala Val Ala Gly Pro Ala Ala
                20                  25                  30

Ala Gln Asn Cys Gly Cys Gln Pro Asn Val Cys Cys Ser Lys Phe Gly
            35                  40                  45

Tyr Cys Gly Thr Thr Asp Glu Tyr Cys Gly Asp Gly Cys Gln Ser Gly
        50                  55                  60

Pro Cys Arg Ser Gly Gly Gly Ser Ser Gly Gly Gly Gly Ala Asn
65                  70                  75                  80

Val Ala Ser Val Val Thr Gly Ser Phe Phe Asn Gly Ile Lys Ser Gln
```

-continued

```
                        85                  90                  95
Ala Gly Ser Gly Cys Glu Gly Lys Asn Phe Tyr Thr Arg Ser Ala Phe
                100                 105                 110

Leu Ser Ala Val Lys Ala Tyr Pro Gly Phe Ala His Gly Gly Ser Gln
            115                 120                 125

Val Gln Gly Lys Arg Glu Ile Ala Ala Phe Phe Ala His Ala Thr His
        130                 135                 140

Glu Thr Gly His Phe Cys Tyr Ile Ser Glu Ile Asn Lys Ser Asn Ala
145                 150                 155                 160

Tyr Cys Asp Pro Thr Lys Arg Gln Trp Pro Cys Ala Ala Gly Gln Lys
                165                 170                 175

Tyr Tyr Gly Arg Gly Pro Leu Gln Ile Ser Trp Asn Tyr Asn Tyr Gly
            180                 185                 190

Pro Ala Gly Arg Ala Ile Gly Phe Asp Gly Leu Gly Asp Pro Gly Arg
        195                 200                 205

Val Ala Arg Asp Ala Val Val Ala Phe Lys Ala Ala Leu Trp Phe Trp
    210                 215                 220

Met Asn Ser Val His Gly Val Val Pro Gln Gly Phe Gly Ala Thr Thr
225                 230                 235                 240

Arg Ala Ile Asn Gly Ala Leu Glu Cys Gly Gly Asn Asn Pro Ala Gln
                245                 250                 255

Met Asn Ala Arg Val Gly Tyr Tyr Arg Gln Tyr Cys Arg Gln Leu Gly
            260                 265                 270

Val Asp Pro Gly Pro Asn Leu Thr Cys
        275                 280

<210> SEQ ID NO 3
<211> LENGTH: 1102
<212> TYPE: DNA
<213> ORGANISM: Zea mays
<220> FEATURE:
<221> NAME/KEY: CDS
<222> LOCATION: (16)...(918)

<400> SEQUENCE: 3
ctccagcaca tagca atg gcg ttc acg cgg cgg cgt ccg tgc ggc atc ctc      51
                Met Ala Phe Thr Arg Arg Arg Pro Cys Gly Ile Leu
                  1               5                  10 ctc ctc tcc ctg ctg gcg gca tcc ggc tcg ctg tcg ctg gcc gcc acc      99
Leu Leu Ser Leu Leu Ala Ala Ser Gly Ser Leu Ser Leu Ala Ala Thr
         15                  20                  25 ggc ccg ggc gac gtg gcc gtc ttc tgg ggc cgg aac aag gac gag ggc     147
Gly Pro Gly Asp Val Ala Val Phe Trp Gly Arg Asn Lys Asp Glu Gly
 30                  35                  40 acg ctg cgc gag gcc tgc gac acg ggc acc tac acc gtc atc atc         195
Thr Leu Arg Glu Ala Cys Asp Thr Gly Thr Tyr Thr Thr Val Ile Ile
 45                  50                  55                  60 tcc ttc ctc cgc ggc ttc ggc cac ggc gcc gcc tac tac tcg ctc gac     243
Ser Phe Leu Arg Gly Phe Gly His Gly Ala Ala Tyr Tyr Ser Leu Asp
                 65                  70                  75 ctc tcg ggc cac ccg ctc gcg ggc gtc ggc gcc gac gtc aag cac tgc     291
Leu Ser Gly His Pro Leu Ala Gly Val Gly Ala Asp Val Lys His Cys
             80                  85                  90 cag gcc aag ggc atc ctc gtg ctc ctc tcc atc ggc ggg ccg ccc aac     339
Gln Ala Lys Gly Ile Leu Val Leu Leu Ser Ile Gly Gly Pro Pro Asn
         95                 100                 105 acc aac acc ggc gcc ggc gcc ggc tac tcc ctc ccg tcc gcg cgg gcg     387
Thr Asn Thr Gly Ala Gly Ala Gly Tyr Ser Leu Pro Ser Ala Arg Ala
```

```
        110                 115                 120
gcg gcg gac ctc gcc gcg tac ctg tgg gac gcc tac ctg ggc ggc tcg    435
Ala Ala Asp Leu Ala Ala Tyr Leu Trp Asp Ala Tyr Leu Gly Gly Ser
125                 130                 135                 140 cgc gcg ggg ctg cgc cgc ccg ttc ggc gac gcg gcg ctg gac ggc gtc    483
Arg Ala Gly Leu Arg Arg Pro Phe Gly Asp Ala Ala Leu Asp Gly Val
            145                 150                 155 gac ctg tac atc gac cag ggc ggc gtc gac ggc cac tac gac gag ctg    531
Asp Leu Tyr Ile Asp Gln Gly Gly Val Asp Gly His Tyr Asp Glu Leu
160                 165                 170 gcc agg cgc ctc tac gcc tac aac agg agc tac cgc ggc agg ctc ggg    579
Ala Arg Arg Leu Tyr Ala Tyr Asn Arg Ser Tyr Arg Gly Arg Leu Gly
        175                 180                 185 gtg acg ctg acg gcc acg gtg cgg tgc gcg tac ccg gac ccg cgc gcg    627
Val Thr Leu Thr Ala Thr Val Arg Cys Ala Tyr Pro Asp Pro Arg Ala
190                 195                 200 cag gcg gcg ctc gcc acg ggg ctc gtc tcc cgc gtc cac gtc cgc ctg    675
Gln Ala Ala Leu Ala Thr Gly Leu Val Ser Arg Val His Val Arg Leu
205                 210                 215                 220 tac ggc gac ctc aag tgc acc tgg tcc gac cgg gag gcg tgg gag aag    723
Tyr Gly Asp Leu Lys Cys Thr Trp Ser Asp Arg Glu Ala Trp Glu Lys
            225                 230                 235 tgg gcc gcg gcg tac ccg gcc agc cgc gtg ttc gtc ggc gtc gtg gcg    771
Trp Ala Ala Ala Tyr Pro Ala Ser Arg Val Phe Val Gly Val Val Ala
        240                 245                 250 tcg ccc gag gcg gac aag gac gcg tac atg ttc cag aag gac ctc tac    819
Ser Pro Glu Ala Asp Lys Asp Ala Tyr Met Phe Gln Lys Asp Leu Tyr
    255                 260                 265 tac aac gtg ctg cag ttc gcc cag aag gcg ccc aac tac ggt ggc ctc    867
Tyr Asn Val Leu Gln Phe Ala Gln Lys Ala Pro Asn Tyr Gly Gly Leu
270                 275                 280 atg atc tgg gat agg tac tac gac aag atg aac cac tac atc agc agc    915
Met Ile Trp Asp Arg Tyr Tyr Asp Lys Met Asn His Tyr Ile Ser Ser
285                 290                 295                 300 agc taataattaa gcttcccatc cacatccatc cacatccacc cggtttatca          968
Ser cctaatatat aatagtatta ttgtattttt cttcttaact ttataataca ctgtaatgta  1028
ataatgtgat gatctgatga tccaccaacg gaataaaatg gtcagcttcc agccaaaaaa  1088
aaaaaaaaaa aaaa                                                    1102

<210> SEQ ID NO 4
<211> LENGTH: 301
<212> TYPE: PRT
<213> ORGANISM: Zea mays

<400> SEQUENCE: 4

Met Ala Phe Thr Arg Arg Pro Cys Gly Ile Leu Leu Leu Ser Leu
 1               5                  10                  15

Leu Ala Ala Ser Gly Ser Leu Ser Leu Ala Ala Thr Gly Pro Gly Asp
            20                  25                  30

Val Ala Val Phe Trp Gly Arg Asn Lys Asp Glu Gly Thr Leu Arg Glu
        35                  40                  45

Ala Cys Asp Thr Gly Thr Tyr Thr Thr Val Ile Ile Ser Phe Leu Arg
    50                  55                  60

Gly Phe Gly His Gly Ala Ala Tyr Tyr Ser Leu Asp Leu Ser Gly His
65                  70                  75                  80

Pro Leu Ala Gly Val Gly Ala Asp Val Lys His Cys Gln Ala Lys Gly
```

```
                     85                  90                  95
Ile Leu Val Leu Leu Ser Ile Gly Gly Pro Pro Asn Thr Asn Thr Gly
                100                 105                 110

Ala Gly Ala Gly Tyr Ser Leu Pro Ser Ala Arg Ala Ala Asp Leu
            115                 120                 125

Ala Ala Tyr Leu Trp Asp Ala Tyr Leu Gly Gly Ser Arg Ala Gly Leu
    130                 135                 140

Arg Arg Pro Phe Gly Asp Ala Ala Leu Asp Gly Val Asp Leu Tyr Ile
145                 150                 155                 160

Asp Gln Gly Gly Val Asp Gly His Tyr Asp Glu Leu Ala Arg Arg Leu
                165                 170                 175

Tyr Ala Tyr Asn Arg Ser Tyr Arg Gly Arg Leu Gly Val Thr Leu Thr
            180                 185                 190

Ala Thr Val Arg Cys Ala Tyr Pro Asp Pro Arg Ala Gln Ala Ala Leu
            195                 200                 205

Ala Thr Gly Leu Val Ser Arg Val His Val Arg Leu Tyr Gly Asp Leu
    210                 215                 220

Lys Cys Thr Trp Ser Asp Arg Glu Ala Trp Lys Trp Ala Ala Ala
225                 230                 235                 240

Tyr Pro Ala Ser Arg Val Phe Val Gly Val Val Ala Ser Pro Glu Ala
            245                 250                 255

Asp Lys Asp Ala Tyr Met Phe Gln Lys Asp Leu Tyr Tyr Asn Val Leu
                260                 265                 270

Gln Phe Ala Gln Lys Ala Pro Asn Tyr Gly Gly Leu Met Ile Trp Asp
            275                 280                 285

Arg Tyr Tyr Asp Lys Met Asn His Tyr Ile Ser Ser Ser
    290                 295                 300

<210> SEQ ID NO 5
<211> LENGTH: 1163
<212> TYPE: DNA
<213> ORGANISM: Zea mays
<220> FEATURE:
<221> NAME/KEY: CDS
<222> LOCATION: (32)...(814)

<400> SEQUENCE: 5
ctaaacaaca ccagcttctc tcacgatcac g atg atg aga gcc ctg gcg gtg        52
                                   Met Met Arg Ala Leu Ala Val
                                    1               5 gtg gcc atg gtg gcc acc gcc tta ttc ttc gct gtg ccc gct cgc gcc      100
Val Ala Met Val Ala Thr Ala Leu Phe Phe Ala Val Pro Ala Arg Ala
        10                  15                  20 gag cag tgc ggg tcg cag gcc ggc ggc gcg ctg tgc ccc aac tgc ctg      148
Glu Gln Cys Gly Ser Gln Ala Gly Gly Ala Leu Cys Pro Asn Cys Leu
 25                  30                  35 tgc tgc agc cag ttc ggg tgg tgc ggc agc acc tcc gac tac tgc ggc      196
Cys Cys Ser Gln Phe Gly Trp Cys Gly Ser Thr Ser Asp Tyr Cys Gly
 40                  45                  50                  55 agc ggt tgc cag agc cag tgc agc ggc agc tgc ggc agc acc ccg aac      244
Ser Gly Cys Gln Ser Gln Cys Ser Gly Ser Cys Gly Ser Thr Pro Asn
                 60                  65                  70 ccg ccg agc agc ggc ggc gtg gcg tcc atc atc ccc gag tcg ctc ttc      292
Pro Pro Ser Ser Gly Gly Val Ala Ser Ile Ile Pro Glu Ser Leu Phe
         75                  80                  85 aac cag atg ctg ctg cac cgc aac gac gcg gcg tgc ccc gcc aac ggc      340
Asn Gln Met Leu Leu His Arg Asn Asp Ala Ala Cys Pro Ala Asn Gly
             90                  95                 100
```

```
ttc tac acc tac gcg ggc ttc atc gcg gcg gcc aac gcg ttc ccg ggc    388
Phe Tyr Thr Tyr Ala Gly Phe Ile Ala Ala Ala Asn Ala Phe Pro Gly
    105                 110                 115 ttc ggc acc acg ggg gcg ccc gac gtg cag aag cgc gag ctg gcg cct    436
Phe Gly Thr Thr Gly Ala Pro Asp Val Gln Lys Arg Glu Leu Ala Pro
120                 125                 130                 135 ggc ggc gtt cct ggc gca gac gtc gca cga gac gac ggg cgg gtg ggc    484
Gly Gly Val Pro Gly Ala Asp Val Ala Arg Asp Asp Gly Arg Val Gly
                140                 145                 150 gac ggc gcc cga cgg gcc cta cgc ctg ggg cta ctg ctt caa gga gga    532
Asp Gly Ala Arg Arg Ala Leu Arg Leu Gly Leu Leu Leu Gln Gly Gly
            155                 160                 165 gca ggg cgg cgc gtc ggg gcc gga cta ctg cga gcc cag cgc cca gtg    580
Ala Gly Arg Arg Val Gly Ala Gly Leu Leu Arg Ala Gln Arg Pro Val
        170                 175                 180 gcc gtg cgc cgc ggg gaa gaa gta cta cgg ccg cgg gcc cat cca gat    628
Ala Val Arg Arg Gly Glu Glu Val Leu Arg Pro Arg Ala His Pro Asp
    185                 190                 195 atc cta caa cta caa cta cgg gcc cgc cgg cca ggc cat cgg cgc cgg    676
Ile Leu Gln Leu Gln Leu Arg Ala Arg Arg Pro Gly His Arg Arg Arg
200                 205                 210                 215 cat cct cgc caa ccc gga cct ggt ggc cac cga ccc cac cgt gtc gtt    724
His Pro Arg Gln Pro Gly Pro Gly Gly His Arg Pro His Arg Val Val
                220                 225                 230 cga gac cgc cgt ctg gtt ctg gat gac gcc gca gtc gcc caa gcc gtc    772
Arg Asp Arg Arg Leu Val Leu Asp Asp Ala Ala Val Ala Gln Ala Val
            235                 240                 245 gtg cca cga cgt cat gac ggg gca gtg gac gcc ctc cgc ggc            814
Val Pro Arg Arg His Asp Gly Ala Val Asp Ala Leu Arg Gly
        250                 255                 260 tgacacggcc gccggcaggc tgccgggcta cggcgtcgtc accaacatca tcaacggcgg    874
cctcgagtgc ggccatggcg ctgacagccg cgtcgccgac cggatcggct tctacaaacg    934
atactgtgac ttgcttgggg tcagctacgg cgacaacttg gactgcgcca accagacgcc    994
cttcaacggc tgattaataa gctagctacc tcaccatgca tgcatgcctt attattagag   1054
aacacaataa gacctgatcg atatgatgat gggtatgtat tactttacta cacgcagatc   1114
cagcaatcaa gaataaagca aattaatgtt aaaaaaaaaa aaaaaaaa              1163
```

<210> SEQ ID NO 6
<211> LENGTH: 261
<212> TYPE: PRT
<213> ORGANISM: Zea mays

<400> SEQUENCE: 6

```
Met Met Arg Ala Leu Ala Val Val Ala Met Val Ala Thr Ala Leu Phe
1               5                   10                  15

Phe Ala Val Pro Ala Arg Ala Glu Gln Cys Gly Ser Gln Ala Gly Gly
                20                  25                  30

Ala Leu Cys Pro Asn Cys Leu Cys Ser Gln Phe Gly Trp Cys Gly
            35                  40                  45

Ser Thr Ser Asp Tyr Cys Gly Ser Gly Cys Gln Ser Gln Cys Ser Gly
        50                  55                  60

Ser Cys Gly Ser Thr Pro Asn Pro Pro Ser Ser Gly Gly Val Ala Ser
65                  70                  75                  80

Ile Ile Pro Glu Ser Leu Phe Asn Gln Met Leu Leu His Arg Asn Asp
                85                  90                  95
```

-continued

```
Ala Ala Cys Pro Ala Asn Gly Phe Tyr Thr Tyr Ala Gly Phe Ile Ala
            100                 105                 110

Ala Ala Asn Ala Phe Pro Gly Phe Gly Thr Thr Gly Ala Pro Asp Val
            115                 120                 125

Gln Lys Arg Glu Leu Ala Pro Gly Gly Val Pro Gly Ala Asp Val Ala
            130                 135                 140

Arg Asp Asp Gly Arg Val Gly Asp Gly Ala Arg Arg Ala Leu Arg Leu
145                 150                 155                 160

Gly Leu Leu Leu Gln Gly Gly Ala Gly Arg Arg Val Gly Ala Gly Leu
                165                 170                 175

Leu Arg Ala Gln Arg Pro Val Ala Val Arg Gly Glu Glu Val Leu
            180                 185                 190

Arg Pro Arg Ala His Pro Asp Ile Leu Gln Leu Gln Leu Arg Ala Arg
            195                 200                 205

Arg Pro Gly His Arg Arg His Pro Arg Gln Pro Gly Pro Gly Gly
            210                 215                 220

His Arg Pro His Arg Val Val Arg Asp Arg Arg Leu Val Leu Asp Asp
225                 230                 235                 240

Ala Ala Val Ala Gln Ala Val Val Pro Arg Arg His Asp Gly Ala Val
                245                 250                 255

Asp Ala Leu Arg Gly
            260

<210> SEQ ID NO 7
<211> LENGTH: 1195
<212> TYPE: DNA
<213> ORGANISM: Zea mays
<220> FEATURE:
<221> NAME/KEY: CDS
<222> LOCATION: (41)...(1009)

<400> SEQUENCE: 7
gagaatttgc gataccgatc tgggagaaga aagggcgtc atg tcg tcg ttc gga       55
                                           Met Ser Ser Phe Gly
                                             1               5 cgc aat tca tgg tgt atc ctc gtg ctg gcc tcc gtg ctc ctc ctg tcc    103
Arg Asn Ser Trp Cys Ile Leu Val Leu Ala Ser Val Leu Leu Leu Ser
            10                  15                  20 tgc ctc gcc gac acg gcc gtg gcc aag cga aca ggc gag ctc acc gtc    151
Cys Leu Ala Asp Thr Ala Val Ala Lys Arg Thr Gly Glu Leu Thr Val
        25                  30                  35 ttc tgg ggc cgg aac aag gag gag ggc aca ctg cgt gag gcc tgc gac    199
Phe Trp Gly Arg Asn Lys Glu Glu Gly Thr Leu Arg Glu Ala Cys Asp
    40                  45                  50 acc ggg ctc tac aac acc gtc atc atc tcc ttc tac agc gtc ttc ggc    247
Thr Gly Leu Tyr Asn Thr Val Ile Ile Ser Phe Tyr Ser Val Phe Gly
55                  60                  65 cac ggc cgc tac gcc ctt gac ctc tcc ggc cac ccg ctg gac ggc gtc    295
His Gly Arg Tyr Ala Leu Asp Leu Ser Gly His Pro Leu Asp Gly Val
        70                  75                  80                  85 ggc gcc gac atc aag cac tgc cag tcc cag ggc atc ccg gtc ttc ctc    343
Gly Ala Asp Ile Lys His Cys Gln Ser Gln Gly Ile Pro Val Phe Leu
                90                  95                 100 tcc atc ggc ggc ggg gga aac cac tac tcc atc cct tcc tcc gcg tcc    391
Ser Ile Gly Gly Gly Gly Asn His Tyr Ser Ile Pro Ser Ser Ala Ser
            105                 110                 115 gcg gag gcc gtc gcg gac aac ctg tgg aac gcg ttc ctc ggc ggc ggc    439
Ala Glu Ala Val Ala Asp Asn Leu Trp Asn Ala Phe Leu Gly Gly Gly
        120                 125                 130
```

```
aac agc gac gtg ccc cgc ccc ttc ggt gac gcg gcg gtc aac ggc atc       487
Asn Ser Asp Val Pro Arg Pro Phe Gly Asp Ala Ala Val Asn Gly Ile
    135                 140                 145 gac ttc tac atc gac gac cac agc gca ccg ggc gac cac tac gac gag       535
Asp Phe Tyr Ile Asp Asp His Ser Ala Pro Gly Asp His Tyr Asp Glu
150                 155                 160                 165 ctc gcg cgc cgt ctc gac tac ttc aac agc atg tac tac cac gcc acg       583
Leu Ala Arg Arg Leu Asp Tyr Phe Asn Ser Met Tyr Tyr His Ala Thr
                170                 175                 180 acg aag tac gta cgg ctg acg gcg acg ccg cgg tgc gcg ttc ccg ccc       631
Thr Lys Tyr Val Arg Leu Thr Ala Thr Pro Arg Cys Ala Phe Pro Pro
            185                 190                 195 gac gac ccc atg gcg cgg gcg ctg cgg acg ggg ctg ttc gag cgc atc       679
Asp Asp Pro Met Ala Arg Ala Leu Arg Thr Gly Leu Phe Glu Arg Ile
        200                 205                 210 cac gtc cgc ttc tac ggc gac gcc gac aag tgc tcg tac aag aac ggc       727
His Val Arg Phe Tyr Gly Asp Ala Asp Lys Cys Ser Tyr Lys Asn Gly
    215                 220                 225 gac gtg tcc ggc gtc gtg gac cag tgg agc aag tgg acg gcg agg tac       775
Asp Val Ser Gly Val Val Asp Gln Trp Ser Lys Trp Thr Ala Arg Tyr
230                 235                 240                 245 ccc aag agc cag ctt tac gtg ggg ctc gcc gcg gcc gag agc ggc gtg       823
Pro Lys Ser Gln Leu Tyr Val Gly Leu Ala Ala Ala Glu Ser Gly Val
                250                 255                 260 ccg gac cac gcg ccg ccc ccc gtt gag gtc tac ctc aaa tac ctc tac       871
Pro Asp His Ala Pro Pro Pro Val Glu Val Tyr Leu Lys Tyr Leu Tyr
            265                 270                 275 tac gat ctg ctg ccc aag gtg cag aag gcg ccc aac tat ggt ggc gtc       919
Tyr Asp Leu Leu Pro Lys Val Gln Lys Ala Pro Asn Tyr Gly Gly Val
        280                 285                 290 atg gtc tgg aat agg ttc acc gac aac agg acc gga tac agc ggc gcc       967
Met Val Trp Asn Arg Phe Thr Asp Asn Arg Thr Gly Tyr Ser Gly Ala
    295                 300                 305 gtc aag ggc tgg gcg gct tgc agc tat gct ggc tgt gtt aac                1009
Val Lys Gly Trp Ala Ala Cys Ser Tyr Ala Gly Cys Val Asn
310                 315                 320 taagtgcata gcgcatgtat aaaccacgta ataattcgt ataaggtgca agtataaata      1069
aacacaagag actttcgtga taatcgaatg tttctttatg tctaaaatac agttccactt     1129
atacaacata aatacattga atgaagtttc ttaaaaaaaa aaaaaaaaaa aaaaaaaaaa     1189
aaaaaa                                                                 1195

<210> SEQ ID NO 8
<211> LENGTH: 323
<212> TYPE: PRT
<213> ORGANISM: Zea mays

<400> SEQUENCE: 8

Met Ser Ser Phe Gly Arg Asn Ser Trp Cys Ile Leu Val Leu Ala Ser
1               5                   10                  15

Val Leu Leu Leu Ser Cys Leu Ala Asp Thr Ala Val Ala Lys Arg Thr
                20                  25                  30

Gly Glu Leu Thr Val Phe Trp Gly Arg Asn Lys Glu Glu Gly Thr Leu
            35                  40                  45

Arg Glu Ala Cys Asp Thr Gly Leu Tyr Asn Thr Val Ile Ile Ser Phe
        50                  55                  60

Tyr Ser Val Phe Gly His Gly Arg Tyr Ala Leu Asp Leu Ser Gly His
65                  70                  75                  80
```

```
Pro Leu Asp Gly Val Gly Ala Asp Ile Lys His Cys Gln Ser Gln Gly
                85                  90                  95

Ile Pro Val Phe Leu Ser Ile Gly Gly Gly Asn His Tyr Ser Ile
            100                 105                 110

Pro Ser Ser Ala Ser Ala Glu Ala Val Ala Asp Asn Leu Trp Asn Ala
        115                 120                 125

Phe Leu Gly Gly Gly Asn Ser Asp Val Pro Arg Pro Phe Gly Asp Ala
    130                 135                 140

Ala Val Asn Gly Ile Asp Phe Tyr Ile Asp His Ser Ala Pro Gly
145                 150                 155                 160

Asp His Tyr Asp Glu Leu Ala Arg Arg Leu Asp Tyr Phe Asn Ser Met
                165                 170                 175

Tyr Tyr His Ala Thr Thr Lys Tyr Val Arg Leu Thr Ala Thr Pro Arg
            180                 185                 190

Cys Ala Phe Pro Pro Asp Asp Pro Met Ala Arg Ala Leu Arg Thr Gly
        195                 200                 205

Leu Phe Glu Arg Ile His Val Arg Phe Tyr Gly Asp Ala Asp Lys Cys
    210                 215                 220

Ser Tyr Lys Asn Gly Asp Val Ser Gly Val Val Asp Gln Trp Ser Lys
225                 230                 235                 240

Trp Thr Ala Arg Tyr Pro Lys Ser Gln Leu Tyr Val Gly Leu Ala Ala
                245                 250                 255

Ala Glu Ser Gly Val Pro Asp His Ala Pro Pro Val Glu Val Tyr
            260                 265                 270

Leu Lys Tyr Leu Tyr Tyr Asp Leu Leu Pro Lys Val Gln Lys Ala Pro
    275                 280                 285

Asn Tyr Gly Gly Val Met Val Trp Asn Arg Phe Thr Asp Asn Arg Thr
290                 295                 300

Gly Tyr Ser Gly Ala Val Lys Gly Trp Ala Ala Cys Ser Tyr Ala Gly
305                 310                 315                 320

Cys Val Asn

<210> SEQ ID NO 9
<211> LENGTH: 1145
<212> TYPE: DNA
<213> ORGANISM: Zea mays
<220> FEATURE:
<221> NAME/KEY: CDS
<222> LOCATION: (48)...(974)

<400> SEQUENCE: 9
ggcaagcagc agtaataaga aaccatcatc gatccatgta tccacca atg gcg gcg     56
                                                   Met Ala Ala
                                                     1 ctc gga gga cga cgg agg agg gcg tcg tca gcc gcc ctc ctg cta gcc   104
Leu Gly Gly Arg Arg Arg Arg Ala Ser Ser Ala Ala Leu Leu Leu Ala
  5                  10                  15 ttg ttg gcg gtg gcc ctg gtc tcc ctg gcc ggc cca gcc acg gcc gcg   152
Leu Leu Ala Val Ala Leu Val Ser Leu Ala Gly Pro Ala Thr Ala Ala
 20                  25                  30                  35 ggg aac aag acc ggg cag gtg acc gtg ttc tgg ggc cgg aac aag gcc   200
Gly Asn Lys Thr Gly Gln Val Thr Val Phe Trp Gly Arg Asn Lys Ala
                 40                  45                  50 gag ggc acg ctg cgc gag gcc tgc gac tcg ggc ctc tac acc atg gtg   248
Glu Gly Thr Leu Arg Glu Ala Cys Asp Ser Gly Leu Tyr Thr Met Val
     55                  60                  65
```

```
atc atg tcc tta ctc gac gtc tac ggc ccg cag cgc ggc ggc tac cac      296
Ile Met Ser Leu Leu Asp Val Tyr Gly Pro Gln Arg Gly Gly Tyr His
         70                  75                  80 cag tac cac ctg gac ctg tcg ggg cac ccg acg gcc ggc atc ggg gac      344
Gln Tyr His Leu Asp Leu Ser Gly His Pro Thr Ala Gly Ile Gly Asp
     85                  90                  95 gac atc aag cac tgc cag ttc gtg ggc gtg ccg gtg acg ctc tcc gtc      392
Asp Ile Lys His Cys Gln Phe Val Gly Val Pro Val Thr Leu Ser Val
100             105                 110                 115 ggc ggc ttc ggc tcc ggc tac tcg ctc ccg tcc acg cag gcg gcg ctg      440
Gly Gly Phe Gly Ser Gly Tyr Ser Leu Pro Ser Thr Gln Ala Ala Leu
            120                 125                 130 gac ctg ttc gac tac ctc tgg aac gcc ttc ctc ggc ggg tcg aag ccg      488
Asp Leu Phe Asp Tyr Leu Trp Asn Ala Phe Leu Gly Gly Ser Lys Pro
        135                 140                 145 ggc gtg cgc cgc ccc ttc ggc gac gcg tgg ctc gac ggc gtc gac ctg      536
Gly Val Arg Arg Pro Phe Gly Asp Ala Trp Leu Asp Gly Val Asp Leu
    150                 155                 160 ttc ctg gag cgc ggc tcg ccc gcc gac cgc tac gac gtg ctg gcg ctc      584
Phe Leu Glu Arg Gly Ser Pro Ala Asp Arg Tyr Asp Val Leu Ala Leu
165                 170                 175 gag ctc gcc aag cac aac atc cgc ggc ggg ccc ggc aag ccg ctg cac      632
Glu Leu Ala Lys His Asn Ile Arg Gly Gly Pro Gly Lys Pro Leu His
180                 185                 190                 195 ctg acg gcc acg ccg cgc tgc ggc ttc ccg ccc gcc ggc tac ctg cgc      680
Leu Thr Ala Thr Pro Arg Cys Gly Phe Pro Pro Ala Gly Tyr Leu Arg
                200                 205                 210 cgc gcg ctc gac acg ggc atc ttc gag cgc gtc cac gtc cgg atc tac      728
Arg Ala Leu Asp Thr Gly Ile Phe Glu Arg Val His Val Arg Ile Tyr
            215                 220                 225 gac gac gcc gac tgc gag gcc agg tgg cac ctc gcg tgg gac gag tgg      776
Asp Asp Ala Asp Cys Glu Ala Arg Trp His Leu Ala Trp Asp Glu Trp
        230                 235                 240 acg gcg gcg tac ccg gcc acc agg ttc tac gtc ggc ctc acg gcg tcg      824
Thr Ala Ala Tyr Pro Ala Thr Arg Phe Tyr Val Gly Leu Thr Ala Ser
    245                 250                 255 gag atg acg cac ggc tgg gtg cac ccc aag aac gtc tac tac gac gtc      872
Glu Met Thr His Gly Trp Val His Pro Lys Asn Val Tyr Tyr Asp Val
260                 265                 270                 275 gcg ccg tcc gcg cag aag gcg gac aac tac ggc ggc ttc atg atc tgg      920
Ala Pro Ser Ala Gln Lys Ala Asp Asn Tyr Gly Gly Phe Met Ile Trp
                280                 285                 290 gac cgc tac tac gac aag ctc tcc aac tac acc agc atg gtc aag gac      968
Asp Arg Tyr Tyr Asp Lys Leu Ser Asn Tyr Thr Ser Met Val Lys Asp
            295                 300                 305 tac gct tgattggatt tctcgactca gttcagagca gacatgcatg ctagctgcgt      1024
Tyr Ala cagccgcttc gatctagctc accgacctat ataagccgaa gtactgtgta gtgtgtttgc      1084
attttattgt aacaaactaa gaaggaataa attggcgaat aaacaaaaaa aaaaaaaaa       1144 a                                                                      1145
```

<210> SEQ ID NO 10
<211> LENGTH: 309
<212> TYPE: PRT
<213> ORGANISM: Zea mays

<400> SEQUENCE: 10

Met Ala Ala Leu Gly Gly Arg Arg Arg Ala Ser Ser Ala Ala Leu
1               5                   10                  15

Leu Leu Ala Leu Leu Ala Val Ala Leu Val Ser Leu Ala Gly Pro Ala
            20                  25                  30

Thr Ala Ala Gly Asn Lys Thr Gly Gln Val Thr Val Phe Trp Gly Arg
        35                  40                  45

Asn Lys Ala Glu Gly Thr Leu Arg Glu Ala Cys Asp Ser Gly Leu Tyr
    50                  55                  60

Thr Met Val Ile Met Ser Leu Leu Asp Val Tyr Gly Pro Gln Arg Gly
65                  70                  75                  80

Gly Tyr His Gln Tyr His Leu Asp Leu Ser Gly His Pro Thr Ala Gly
                85                  90                  95

Ile Gly Asp Asp Ile Lys His Cys Gln Phe Val Gly Val Pro Val Thr
            100                 105                 110

Leu Ser Val Gly Gly Phe Gly Ser Gly Tyr Ser Leu Pro Ser Thr Gln
        115                 120                 125

Ala Ala Leu Asp Leu Phe Asp Tyr Leu Trp Asn Ala Phe Leu Gly Gly
    130                 135                 140

Ser Lys Pro Gly Val Arg Arg Pro Phe Gly Asp Ala Trp Leu Asp Gly
145                 150                 155                 160

Val Asp Leu Phe Leu Glu Arg Gly Ser Pro Ala Asp Arg Tyr Asp Val
                165                 170                 175

Leu Ala Leu Glu Leu Ala Lys His Asn Ile Arg Gly Gly Pro Gly Lys
            180                 185                 190

Pro Leu His Leu Thr Ala Thr Pro Arg Cys Gly Phe Pro Pro Ala Gly
        195                 200                 205

Tyr Leu Arg Arg Ala Leu Asp Thr Gly Ile Phe Glu Arg Val His Val
    210                 215                 220

Arg Ile Tyr Asp Asp Ala Asp Cys Glu Ala Arg Trp His Leu Ala Trp
225                 230                 235                 240

Asp Glu Trp Thr Ala Ala Tyr Pro Ala Thr Arg Phe Tyr Val Gly Leu
                245                 250                 255

Thr Ala Ser Glu Met Thr His Gly Trp Val His Pro Lys Asn Val Tyr
            260                 265                 270

Tyr Asp Val Ala Pro Ser Ala Gln Lys Ala Asp Asn Tyr Gly Gly Phe
        275                 280                 285

Met Ile Trp Asp Arg Tyr Tyr Asp Lys Leu Ser Asn Tyr Thr Ser Met
    290                 295                 300

Val Lys Asp Tyr Ala
305

<210> SEQ ID NO 11
<211> LENGTH: 1619
<212> TYPE: DNA
<213> ORGANISM: Zea mays
<220> FEATURE:
<221> NAME/KEY: CDS
<222> LOCATION: (315)...(1298)

<400> SEQUENCE: 11
ctgagttgct gcctgcccgg gcgcgtctcc ccctgacag cctcccgcca ccgacaccca     60
catctctccc cgtcggcaca tgtgtagttg ccacttcgct ttcccgtttc tctcaccta    120 cctcacactc ctctccatcg attaatctcc tccccctcaa caaccgcgag atcttcagct   180
accgctctct ccggtcgcgt ttgcatccgc attcctcaga tccagattcg agccccagcc   240
ccgcttcgag atccagctag ctctctatca agcatccggc ggagcgagca gcgggggct    300

-continued

| | |
|---|---|
| cggcgagaga gaag atg aag cgg aag acg cgg aac aag atc atc gta tgg<br>          Met Lys Arg Lys Thr Arg Asn Lys Ile Ile Val Trp<br>           1               5                   10 | 350 |
| acg ctg gcc ctg gct gca gtg gcg att ctg gtg ggc ggc acg att gcg<br>Thr Leu Ala Leu Ala Ala Val Ala Ile Leu Val Gly Gly Thr Ile Ala<br>     15                  20                  25 | 398 |
| ctg gtg ctc acg gcg ggg acg tgg aag gcc aag ata aag aag tcg cag<br>Leu Val Leu Thr Ala Gly Thr Trp Lys Ala Lys Ile Lys Lys Ser Gln<br> 30                  35                  40 | 446 |
| gag aag atc tgt aac aag ggg tgg gag tgc tcg ggg agc aag tac tgc<br>Glu Lys Ile Cys Asn Lys Gly Trp Glu Cys Ser Gly Ser Lys Tyr Cys<br> 45                  50                  55                  60 | 494 |
| tgc aac gac acc atc acc gac ttc ttc aag gtg tac aag ttc gag aac<br>Cys Asn Asp Thr Ile Thr Asp Phe Phe Lys Val Tyr Lys Phe Glu Asn<br>                 65                  70                  75 | 542 |
| ctc ttc gcc aag cgc aac acc ccc gtc gcg cac gcc gtc ggg ttc tgg<br>Leu Phe Ala Lys Arg Asn Thr Pro Val Ala His Ala Val Gly Phe Trp<br>         80                  85                  90 | 590 |
| gac tac cag gcc ttc atc acc gcc gcg gcc ctc ttc gag ccc cag ggg<br>Asp Tyr Gln Ala Phe Ile Thr Ala Ala Ala Leu Phe Glu Pro Gln Gly<br>             95                 100                 105 | 638 |
| ttc tgc acc acc ggc ggc aag cag atg cag atg atg gag ctc tgc gcc<br>Phe Cys Thr Thr Gly Gly Lys Gln Met Gln Met Met Glu Leu Cys Ala<br>         110                 115                 120 | 686 |
| ttc ctc ggg cac gtc ggc gcc aag act tca tgt ggg tac ggc gtg gcg<br>Phe Leu Gly His Val Gly Ala Lys Thr Ser Cys Gly Tyr Gly Val Ala<br>125                 130                 135                 140 | 734 |
| acc ggc ggg ccg acg gcg tgg ggg ctg tgc tac aac cac gag atg agc<br>Thr Gly Gly Pro Thr Ala Trp Gly Leu Cys Tyr Asn His Glu Met Ser<br>                 145                 150                 155 | 782 |
| ccc gac cag acc tac tgc gac aag acc tac acc cag tac ccc tgc gtc<br>Pro Asp Gln Thr Tyr Cys Asp Lys Thr Tyr Thr Gln Tyr Pro Cys Val<br>             160                 165                 170 | 830 |
| gag ggc gcc gag tac tac ggc cga ggc gcg att cct gtc tac tgg aac<br>Glu Gly Ala Glu Tyr Tyr Gly Arg Gly Ala Ile Pro Val Tyr Trp Asn<br>         175                 180                 185 | 878 |
| tac aac tac ggc gct gcc ggt gac ggg atc aag gcg gat ctg ctc cac<br>Tyr Asn Tyr Gly Ala Ala Gly Asp Gly Ile Lys Ala Asp Leu Leu His<br>     190                 195                 200 | 926 |
| cac cca gag tac ctg gag cag aac gcg acg ctg gca ttc atg gcg gcg<br>His Pro Glu Tyr Leu Glu Gln Asn Ala Thr Leu Ala Phe Met Ala Ala<br>205                 210                 215                 220 | 974 |
| atg tgg cgg tgg atg acg ccg atc aag aag agc cag ccg tcg gcg cac<br>Met Trp Arg Trp Met Thr Pro Ile Lys Lys Ser Gln Pro Ser Ala His<br>                 225                 230                 235 | 1022 |
| gac gcc ttc gtg ggc aac tgg aag ccc acc aag aac gac acg ctc agc<br>Asp Ala Phe Val Gly Asn Trp Lys Pro Thr Lys Asn Asp Thr Leu Ser<br>             240                 245                 250 | 1070 |
| aaa cgc ctg cct ggg ttc ggc gcc acc atg aac ata ctc tac ggc gag<br>Lys Arg Leu Pro Gly Phe Gly Ala Thr Met Asn Ile Leu Tyr Gly Glu<br>         255                 260                 265 | 1118 |
| tcg atc tgc ggc aag gga tac gtc gac gcc atg aac gtt ata atc tcg<br>Ser Ile Cys Gly Lys Gly Tyr Val Asp Ala Met Asn Val Ile Ile Ser<br>     270                 275                 280 | 1166 |
| cac tac cag tat tac ctt gat ctc atg ggc gtc ggc cgt gag cac tct<br>His Tyr Gln Tyr Tyr Leu Asp Leu Met Gly Val Gly Arg Glu His Ser<br>285                 290                 295                 300 | 1214 |
| ggc gac aac cgt gat tgc gcc gag cag gca ccg ttc aac ccc tcc agc<br>Gly Asp Asn Arg Asp Cys Ala Glu Gln Ala Pro Phe Asn Pro Ser Ser<br>                 305                 310                 315 | 1262 |

```
ccg acg gat gac cag aag cag cag caa tca gga agc taagacggac    1308
Pro Thr Asp Asp Gln Lys Gln Gln Gln Ser Gly Ser
        320                 325 tcattgcgcc attgccactg atcaagcttc cacagcgcta gattgagcta cagattcttc    1368
aggatgcgtg aagctgcatg catcgtgttg atgttgtttt gaatagactg tatgtactgt    1428
ctatgtgaat tgcgagattt gtggttattt actaccatgt tgtccataga tagtctgttt    1488
tggtttcttt ggttctgtca gatacgttat acacatgttt aaagagaact gaacatacca    1548 ggacccttt  tccgcttgaa aaaaaaaaa  aaaaaaaaaa aaaaaaaaaa aaaaaaaaaa    1608
aaaaaaaaaa a                                                          1619

<210> SEQ ID NO 12
<211> LENGTH: 328
<212> TYPE: PRT
<213> ORGANISM: Zea mays

<400> SEQUENCE: 12

Met Lys Arg Lys Thr Arg Asn Lys Ile Ile Val Trp Thr Leu Ala Leu
 1               5                  10                  15

Ala Ala Val Ala Ile Leu Val Gly Gly Thr Ile Ala Leu Val Leu Thr
                20                  25                  30

Ala Gly Thr Trp Lys Ala Lys Ile Lys Lys Ser Gln Glu Lys Ile Cys
            35                  40                  45

Asn Lys Gly Trp Glu Cys Ser Gly Ser Lys Tyr Cys Cys Asn Asp Thr
    50                  55                  60

Ile Thr Asp Phe Phe Lys Val Tyr Lys Phe Glu Asn Leu Phe Ala Lys
65                  70                  75                  80

Arg Asn Thr Pro Val Ala His Ala Val Gly Phe Trp Asp Tyr Gln Ala
                85                  90                  95

Phe Ile Thr Ala Ala Ala Leu Phe Glu Pro Gln Gly Phe Cys Thr Thr
            100                 105                 110

Gly Gly Lys Gln Met Gln Met Met Glu Leu Cys Ala Phe Leu Gly His
        115                 120                 125

Val Gly Ala Lys Thr Ser Cys Gly Tyr Gly Val Ala Thr Gly Gly Pro
    130                 135                 140

Thr Ala Trp Gly Leu Cys Tyr Asn His Glu Met Ser Pro Asp Gln Thr
145                 150                 155                 160

Tyr Cys Asp Lys Thr Tyr Thr Gln Tyr Pro Cys Val Glu Gly Ala Glu
                165                 170                 175

Tyr Tyr Gly Arg Gly Ala Ile Pro Val Tyr Trp Asn Tyr Asn Tyr Gly
            180                 185                 190

Ala Ala Gly Asp Gly Ile Lys Ala Asp Leu Leu His His Pro Glu Tyr
        195                 200                 205

Leu Glu Gln Asn Ala Thr Leu Ala Phe Met Ala Ala Met Trp Arg Trp
    210                 215                 220

Met Thr Pro Ile Lys Lys Ser Gln Pro Ser Ala His Asp Ala Phe Val
225                 230                 235                 240

Gly Asn Trp Lys Pro Thr Lys Asn Asp Thr Leu Ser Lys Arg Leu Pro
                245                 250                 255

Gly Phe Gly Ala Thr Met Asn Ile Leu Tyr Gly Glu Ser Ile Cys Gly
            260                 265                 270

Lys Gly Tyr Val Asp Ala Met Asn Val Ile Ile Ser His Tyr Gln Tyr
        275                 280                 285
```

```
Tyr Leu Asp Leu Met Gly Val Gly Arg Glu His Ser Gly Asp Asn Arg
    290                 295                 300

Asp Cys Ala Glu Gln Ala Pro Phe Asn Pro Ser Ser Pro Thr Asp Asp
305                 310                 315                 320

Gln Lys Gln Gln Gln Ser Gly Ser
                325

<210> SEQ ID NO 13
<211> LENGTH: 1140
<212> TYPE: DNA
<213> ORGANISM: Zea mays
<220> FEATURE:
<221> NAME/KEY: CDS
<222> LOCATION: (21)...(923)

<400> SEQUENCE: 13
gaagcagcca gtttccgtca atg gca ctg gcc atg gcc acg gtg ctg atg gca      53
                     Met Ala Leu Ala Met Ala Thr Val Leu Met Ala
                       1               5                      10 ctg ggc ggg gta gcc gcc aca gcg cgc gcc ggc ggc ggc atc gcc atc      101
Leu Gly Gly Val Ala Ala Thr Ala Arg Ala Gly Gly Gly Ile Ala Ile
             15                  20                  25 tac tgg ggc cag aac ggc aac gag ggg acg ctg gcg cag acc tgc gcc      149
Tyr Trp Gly Gln Asn Gly Asn Glu Gly Thr Leu Ala Gln Thr Cys Ala
         30                  35                  40 acg ggc aac tac agg ttc gtc aac gtg gcc ttc ctc ccg acg ttc ggc      197
Thr Gly Asn Tyr Arg Phe Val Asn Val Ala Phe Leu Pro Thr Phe Gly
     45                  50                  55 agg ggc cag acg ccg gcg ctg aac ctg gcg ggc cac tgc gac ccg gcg      245
Arg Gly Gln Thr Pro Ala Leu Asn Leu Ala Gly His Cys Asp Pro Ala
 60                  65                  70                  75 agc ggc ggg tgc acg ggc gtg ggc gcg gac gtc aag gcg tgc cag cgc      293
Ser Gly Gly Cys Thr Gly Val Gly Ala Asp Val Lys Ala Cys Gln Arg
                 80                  85                  90 atg ggc gtc aag gtc ctc ctc tcc atc ggc ggg ggc gtc ggc agc tac      341
Met Gly Val Lys Val Leu Leu Ser Ile Gly Gly Gly Val Gly Ser Tyr
             95                 100                 105 ggc ctc tcg tcc cgg gcc gac gcc cgg agc gtc gcg gcg tac ctc tgg      389
Gly Leu Ser Ser Arg Ala Asp Ala Arg Ser Val Ala Ala Tyr Leu Trp
         110                 115                 120 gac aac tac ctc ggc ggc ggg tcc gag tcc agg ccc ctc ggc gac          437
Asp Asn Tyr Leu Gly Gly Gly Ser Glu Ser Arg Pro Leu Gly Asp
125                 130                 135 gcc gtc ctc gac ggc gtc gac ttc gac atc gag agc ggc ggg ggc atg      485
Ala Val Leu Asp Gly Val Asp Phe Asp Ile Glu Ser Gly Gly Gly Met
140                 145                 150                 155 tac tgg gac gac ctg gcc cgg ttc ctc aag tcc tac tcc cgg cgc ggg      533
Tyr Trp Asp Asp Leu Ala Arg Phe Leu Lys Ser Tyr Ser Arg Arg Gly
             160                 165                 170 cgc ggg cgc gcg cgg agg ccc gtg tac ctg tcg gcg gcg ccg cag tgc      581
Arg Gly Arg Ala Arg Arg Pro Val Tyr Leu Ser Ala Ala Pro Gln Cys
         175                 180                 185 ccg ttc ccg gac gcg tcg ctg ggc acc gcg ctc gcc acg ggg ctg ttc      629
Pro Phe Pro Asp Ala Ser Leu Gly Thr Ala Leu Ala Thr Gly Leu Phe
     190                 195                 200 gac tac gtg tgg gtg cag ttc tac aac aac ccg ccg tgc cag tac agc      677
Asp Tyr Val Trp Val Gln Phe Tyr Asn Asn Pro Pro Cys Gln Tyr Ser
205                 210                 215 gcg agc gcc ggc gtg ggc agc ctg gcg caa gcg tgg gcg cag tgg acg      725
Ala Ser Ala Gly Val Gly Ser Leu Ala Gln Ala Trp Ala Gln Trp Thr
220                 225                 230                 235
```

```
tcc atc agg gcg ggg cgg gtg ttc ctc ggc ctc ccc gcc gcg ccc cag    773
Ser Ile Arg Ala Gly Arg Val Phe Leu Gly Leu Pro Ala Ala Pro Gln
            240                 245                 250 gcc gct ggc agc ggg ttc gtg ccg gcg agc gac ctc gtg gcg cag gtg    821
Ala Ala Gly Ser Gly Phe Val Pro Ala Ser Asp Leu Val Ala Gln Val
                255                 260                 265 ctg ccg gtg gtc aag aac tcc acc aag tac ggg ggc atc atg ctc tgg    869
Leu Pro Val Val Lys Asn Ser Thr Lys Tyr Gly Gly Ile Met Leu Trp
        270                 275                 280 tcg agg tac tac gac ggg ctc acg ggg tac agc gac gcg gtc aag tcc    917
Ser Arg Tyr Tyr Asp Gly Leu Thr Gly Tyr Ser Asp Ala Val Lys Ser
285                 290                 295 tac gtg tgagctaggc agcctcgtgt catgtcgggc gtgcaggagg gagtaggact      973
Tyr Val
300 gtaggaggca catgcttcca tgtgcgtgca cgtgcgggc gttatcatac ctatgggtat   1033 actgggtcgc tattcgctaa ggaagagact ggaagaagc aaatcgcaaa tacagcttct   1093 tactactact ttgcaaactt cagttcgttt cggaaaaaaa aaaaaaa               1140

<210> SEQ ID NO 14
<211> LENGTH: 301
<212> TYPE: PRT
<213> ORGANISM: Zea mays

<400> SEQUENCE: 14

Met Ala Leu Ala Met Ala Thr Val Leu Met Ala Leu Gly Gly Val Ala
1               5                   10                  15

Ala Thr Ala Arg Ala Gly Gly Ile Ala Ile Tyr Trp Gly Gln Asn
            20                  25                  30

Gly Asn Glu Gly Thr Leu Ala Gln Thr Cys Ala Thr Gly Asn Tyr Arg
        35                  40                  45

Phe Val Asn Val Ala Phe Leu Pro Thr Phe Gly Arg Gly Gln Thr Pro
    50                  55                  60

Ala Leu Asn Leu Ala Gly His Cys Asp Pro Ala Ser Gly Gly Cys Thr
65                  70                  75                  80

Gly Val Gly Ala Asp Val Lys Ala Cys Gln Arg Met Gly Val Lys Val
                85                  90                  95

Leu Leu Ser Ile Gly Gly Gly Val Gly Ser Tyr Gly Leu Ser Ser Arg
            100                 105                 110

Ala Asp Ala Arg Ser Val Ala Ala Tyr Leu Trp Asp Asn Tyr Leu Gly
        115                 120                 125

Gly Gly Gly Ser Glu Ser Arg Pro Leu Gly Asp Ala Val Leu Asp Gly
    130                 135                 140

Val Asp Phe Asp Ile Glu Ser Gly Gly Gly Met Tyr Trp Asp Asp Leu
145                 150                 155                 160

Ala Arg Phe Leu Lys Ser Tyr Ser Arg Arg Gly Arg Gly Arg Ala Arg
                165                 170                 175

Arg Pro Val Tyr Leu Ser Ala Ala Pro Gln Cys Pro Phe Pro Asp Ala
            180                 185                 190

Ser Leu Gly Thr Ala Leu Ala Thr Gly Leu Phe Asp Tyr Val Trp Val
        195                 200                 205

Gln Phe Tyr Asn Asn Pro Pro Cys Gln Tyr Ser Ala Ser Ala Gly Val
    210                 215                 220

Gly Ser Leu Ala Gln Ala Trp Ala Gln Trp Thr Ser Ile Arg Ala Gly
225                 230                 235                 240
```

```
Arg Val Phe Leu Gly Leu Pro Ala Ala Pro Gln Ala Gly Ser Gly
            245                 250                 255

Phe Val Pro Ala Ser Asp Leu Val Ala Gln Val Leu Pro Val Val Lys
            260                 265                 270

Asn Ser Thr Lys Tyr Gly Gly Ile Met Leu Trp Ser Arg Tyr Tyr Asp
        275                 280                 285

Gly Leu Thr Gly Tyr Ser Asp Ala Val Lys Ser Tyr Val
        290                 295                 300

<210> SEQ ID NO 15
<211> LENGTH: 1085
<212> TYPE: DNA
<213> ORGANISM: Zea mays
<220> FEATURE:
<221> NAME/KEY: CDS
<222> LOCATION: (46)...(966)

<400> SEQUENCE: 15
ggcacgagcg agtagtggta gcagcaatta accaacgaga cacca atg gcg gtc gca      57
                                                  Met Ala Val Ala
                                                    1 agt aat aga cca gca acc act cta ctg ccc ctg gcg gcc ctt gtg gcc     105
Ser Asn Arg Pro Ala Thr Thr Leu Leu Pro Leu Ala Ala Leu Val Ala
  5              10                  15                  20 gtc gct ggc tcc ctc ttc ctc gcc ggc ccg gcc gcg gcc gcg ggg aag     153
Val Ala Gly Ser Leu Phe Leu Ala Gly Pro Ala Ala Ala Ala Gly Lys
                 25                  30                  35 acc ggg cag gtg act gtc ttc tgg ggc cgg aac aag gcc gag ggc acg     201
Thr Gly Gln Val Thr Val Phe Trp Gly Arg Asn Lys Ala Glu Gly Thr
             40                  45                  50 ctc cga gag gcc tgc gac acg ggc acg tac acc atc gtc gtc atc tcc     249
Leu Arg Glu Ala Cys Asp Thr Gly Thr Tyr Thr Ile Val Val Ile Ser
         55                  60                  65 ttc ctc aac gtc tcg gcc ggc ccc ggc aac agc ccg ccg agc ctg gac     297
Phe Leu Asn Val Ser Ala Gly Pro Gly Asn Ser Pro Pro Ser Leu Asp
     70                  75                  80 ctc tcg ggc cac ccc gtc gcc ggc atc ggc gcc gac atc aag cac tgc     345
Leu Ser Gly His Pro Val Ala Gly Ile Gly Ala Asp Ile Lys His Cys
 85                  90                  95                 100 cag tcg aag agc atc atg gtg ttc ctc tcc ctc ggc ggc cgg cag cac     393
Gln Ser Lys Ser Ile Met Val Phe Leu Ser Leu Gly Gly Arg Gln His
                105                 110                 115 tcc ctg ccg agc gcc gag gcc gcc gcg gac ctc gcc gac tac ctc tgg     441
Ser Leu Pro Ser Ala Glu Ala Ala Ala Asp Leu Ala Asp Tyr Leu Trp
            120                 125                 130 tac gcc tac ttc ccg gcg ccg gcg ccg cgc gcc ggc gtg cgc cgc ccg     489
Tyr Ala Tyr Phe Pro Ala Pro Ala Pro Arg Ala Gly Val Arg Arg Pro
        135                 140                 145 ttc ggc gac gcg tac gtc gac ggc ctc gac ttc ttc ctc gac cgc ggc     537
Phe Gly Asp Ala Tyr Val Asp Gly Leu Asp Phe Phe Leu Asp Arg Gly
    150                 155                 160 ggc cgc ccg ccg ccg gac cac ctc gac gcg ctg gcc gcg cgc ctg tgg     585
Gly Arg Pro Pro Pro Asp His Leu Asp Ala Leu Ala Ala Arg Leu Trp
165                 170                 175                 180 agc tac aac cgg cag ttc cgc gcc cgc acg ccc gtg cag ctg tcg gcg     633
Ser Tyr Asn Arg Gln Phe Arg Ala Arg Thr Pro Val Gln Leu Ser Ala
                185                 190                 195 acg ccg cgg tgc gcg ttc ccg ccg gac ggg ccg gcg ctg cgg ctg ctc     681
Thr Pro Arg Cys Ala Phe Pro Pro Asp Gly Pro Ala Leu Arg Leu Leu
            200                 205                 210
```

-continued

```
gcc acg ggg ctc gtt acc cgc gtc aac gtc agg ctc tac ggc gac gcg      729
Ala Thr Gly Leu Val Thr Arg Val Asn Val Arg Leu Tyr Gly Asp Ala
        215                 220                 225 cgc tgc gcc gcg tac tgg cag cag gag tgg gac aag tgg gcc gcg gcg      777
Arg Cys Ala Ala Tyr Trp Gln Gln Glu Trp Asp Lys Trp Ala Ala Ala
230                 235                 240 tac ccg ggc tcc ggg ctc tac gtc ggc ctg ccg gcg tcg gag cgg acg      825
Tyr Pro Gly Ser Gly Leu Tyr Val Gly Leu Pro Ala Ser Glu Arg Thr
245                 250                 255                 260 gtc ggg tac gtc cac ccc aag aac ctg tac tac ggc gtc ctc ccg gtg      873
Val Gly Tyr Val His Pro Lys Asn Leu Tyr Tyr Gly Val Leu Pro Val
                265                 270                 275 gtg cag aag gcg ccc agc tac gcc ggg atc atg atc tgg gac cgc tac      921
Val Gln Lys Ala Pro Ser Tyr Ala Gly Ile Met Ile Trp Asp Arg Tyr
            280                 285                 290 gcc gac aag cag acc aac tac agc agc tac gcc att caa tgg gct          966
Ala Asp Lys Gln Thr Asn Tyr Ser Ser Tyr Ala Ile Gln Trp Ala
                295                 300                 305 tgacactacg agacaaacc ccagaggatc agagcttaat aaataaacaa acaaataaat    1026
ccaagaagtt tagcaagcag ccatatattt atacaattga caaaaaaaaa aaaaaaaaa    1085
```

<210> SEQ ID NO 16
<211> LENGTH: 307
<212> TYPE: PRT
<213> ORGANISM: Zea mays

<400> SEQUENCE: 16

```
Met Ala Val Ala Ser Asn Arg Pro Ala Thr Thr Leu Pro Leu Ala
 1               5                  10                  15

Ala Leu Val Ala Val Ala Gly Ser Leu Phe Leu Ala Gly Pro Ala Ala
            20                  25                  30

Ala Ala Gly Lys Thr Gly Gln Val Thr Val Phe Trp Gly Arg Asn Lys
        35                  40                  45

Ala Glu Gly Thr Leu Arg Glu Ala Cys Asp Thr Gly Thr Tyr Thr Ile
    50                  55                  60

Val Val Ile Ser Phe Leu Asn Val Ser Ala Gly Pro Gly Asn Ser Pro
65                  70                  75                  80

Pro Ser Leu Asp Leu Ser Gly His Pro Val Ala Gly Ile Gly Ala Asp
                85                  90                  95

Ile Lys His Cys Gln Ser Lys Ser Ile Met Val Phe Leu Ser Leu Gly
            100                 105                 110

Gly Arg Gln His Ser Leu Pro Ser Ala Glu Ala Ala Asp Leu Ala
        115                 120                 125

Asp Tyr Leu Trp Tyr Ala Tyr Phe Pro Ala Pro Ala Arg Ala Gly
    130                 135                 140

Val Arg Arg Pro Phe Gly Asp Ala Tyr Val Asp Gly Leu Asp Phe Phe
145                 150                 155                 160

Leu Asp Arg Gly Gly Arg Pro Pro Asp His Leu Asp Ala Leu Ala
                165                 170                 175

Ala Arg Leu Trp Ser Tyr Asn Arg Gln Phe Arg Ala Arg Thr Pro Val
            180                 185                 190

Gln Leu Ser Ala Thr Pro Arg Cys Ala Phe Pro Pro Asp Gly Pro Ala
        195                 200                 205

Leu Arg Leu Leu Ala Thr Gly Leu Val Thr Arg Val Asn Val Arg Leu
    210                 215                 220
```

```
Tyr Gly Asp Ala Arg Cys Ala Ala Tyr Trp Gln Gln Glu Trp Asp Lys
225                 230                 235                 240

Trp Ala Ala Ala Tyr Pro Gly Ser Gly Leu Tyr Val Gly Leu Pro Ala
            245                 250                 255

Ser Glu Arg Thr Val Gly Tyr Val His Pro Lys Asn Leu Tyr Tyr Gly
            260                 265                 270

Val Leu Pro Val Val Gln Lys Ala Pro Ser Tyr Ala Gly Ile Met Ile
            275                 280                 285

Trp Asp Arg Tyr Ala Asp Lys Gln Thr Asn Tyr Ser Ser Tyr Ala Ile
    290                 295                 300

Gln Trp Ala
305

<210> SEQ ID NO 17
<211> LENGTH: 1077
<212> TYPE: DNA
<213> ORGANISM: Zea mays
<220> FEATURE:
<221> NAME/KEY: CDS
<222> LOCATION: (47)...(823)

<400> SEQUENCE: 17
cccacgcgtc cgcccacgcg tccggagagc gcgaagttaa gccacc atg tgg acg        55
                                                 Met Trp Thr
                                                  1 agg gct tta gcg acg gtg ctg ttc gtg gca ggc gcc gcg ctg ctc ggc      103
Arg Ala Leu Ala Thr Val Leu Phe Val Ala Gly Ala Ala Leu Leu Gly
  5                  10                  15 gtc ggc gtc ggc ggc gcc agc gcg cag cag ggc gtg tgg agc atc atc      151
Val Gly Val Gly Gly Ala Ser Ala Gln Gln Gly Val Trp Ser Ile Ile
 20                  25                  30                  35 act cgt ccc atg ttc cag agc atg ctg agc cac cgc ggc gat agc ggg      199
Thr Arg Pro Met Phe Gln Ser Met Leu Ser His Arg Gly Asp Ser Gly
                 40                  45                  50 tgc cag ggc gcc ttc tac acc tac gac gcc ttc atc gag gcc gcc agc      247
Cys Gln Gly Ala Phe Tyr Thr Tyr Asp Ala Phe Ile Glu Ala Ala Ser
         55                  60                  65 aag ttc ccc ggc ttc ggc acc acc ggc gac gag cag acg cgc agg cgg      295
Lys Phe Pro Gly Phe Gly Thr Thr Gly Asp Glu Gln Thr Arg Arg Arg
     70                  75                  80 gag ctc gcc gcc ttc ttc ggc cag acg tcc cac gaa acc acc ggt gga      343
Glu Leu Ala Ala Phe Phe Gly Gln Thr Ser His Glu Thr Thr Gly Gly
 85                  90                  95 tgg gcg act gct ccg ggt gga ccg ttt gcc tgg gga tac tgc cgg gtg      391
Trp Ala Thr Ala Pro Gly Gly Pro Phe Ala Trp Gly Tyr Cys Arg Val
100                 105                 110                 115 aag gaa cag aac ccg acg gac cca ccc tac tat gga cga gga ccc ata      439
Lys Glu Gln Asn Pro Thr Asp Pro Pro Tyr Tyr Gly Arg Gly Pro Ile
                120                 125                 130 cag cta act cat gag tac aac tac agg ctc gcc ggg caa gcg ctg aac      487
Gln Leu Thr His Glu Tyr Asn Tyr Arg Leu Ala Gly Gln Ala Leu Asn
            135                 140                 145 ctg aac ctg gtg ggc aac ccg gac ctg gtg gcg agc gac ccc gtg gta      535
Leu Asn Leu Val Gly Asn Pro Asp Leu Val Ala Ser Asp Pro Val Val
        150                 155                 160 gcc ttc aag acg gcc atc tgg ttc tgg atg acg ccg cag tcg ccc aag      583
Ala Phe Lys Thr Ala Ile Trp Phe Trp Met Thr Pro Gln Ser Pro Lys
    165                 170                 175 ccg tcg tgc cac gcc gtg atg acc ggc gcc tgg acg ccg tcc gcc acc      631
Pro Ser Cys His Ala Val Met Thr Gly Ala Trp Thr Pro Ser Ala Thr
```

-continued

```
                180                 185                 190                 195
gac cgc gcc gcc ggg agg ctc ccc gga tat ggc ctc acc tcg aac atc        679
Asp Arg Ala Ala Gly Arg Leu Pro Gly Tyr Gly Leu Thr Ser Asn Ile
                200                 205                 210 atc aac ggc ggg cta gag tgc ggc aag ggc cag tcc acc gac ggc gcc        727
Ile Asn Gly Gly Leu Glu Cys Gly Lys Gly Gln Ser Thr Asp Gly Ala
                215                 220                 225 aag gac cgg gtc ggc tac tac aag agg tac tgc gat atg ctc cgg gtg        775
Lys Asp Arg Val Gly Tyr Tyr Lys Arg Tyr Cys Asp Met Leu Arg Val
            230                 235                 240 ggg tac ggg gac aac gtg ccc tgc aag gac cag aag cct tac gga gga        823
Gly Tyr Gly Asp Asn Val Pro Cys Lys Asp Gln Lys Pro Tyr Gly Gly
            245                 250                 255 tgaggacgta cgtggacaac aataattata tggttgctgc aagccttcac gtgttttgt        883 tgcctctacc tactaagaat aaatcaagta gcagcaaaca ggggcaacct gctaccttcg        943
gcgtgtgttt tacttatcat atagtgtgtc tatgtatgac acagtatgag ggatgatgta       1003
ctgtctcatc tctggatgca tcataacgaa ctaatcaacg gttagcagca ttcaccttta       1063
aaaaaaaaaa aaaa                                                         1077
```

<210> SEQ ID NO 18
<211> LENGTH: 259
<212> TYPE: PRT
<213> ORGANISM: Zea mays

<400> SEQUENCE: 18

```
Met Trp Thr Arg Ala Leu Ala Thr Val Leu Phe Val Ala Gly Ala Ala
  1               5                  10                  15

Leu Leu Gly Val Gly Val Gly Ala Ser Ala Gln Gln Gly Val Trp
             20                  25                  30

Ser Ile Ile Thr Arg Pro Met Phe Gln Ser Met Leu Ser His Arg Gly
         35                  40                  45

Asp Ser Gly Cys Gln Gly Ala Phe Tyr Thr Tyr Asp Ala Phe Ile Glu
     50                  55                  60

Ala Ala Ser Lys Phe Pro Gly Phe Gly Thr Thr Gly Asp Glu Gln Thr
 65                  70                  75                  80

Arg Arg Arg Glu Leu Ala Ala Phe Phe Gly Gln Thr Ser His Glu Thr
                 85                  90                  95

Thr Gly Gly Trp Ala Thr Ala Pro Gly Gly Pro Phe Ala Trp Gly Tyr
            100                 105                 110

Cys Arg Val Lys Glu Gln Asn Pro Thr Asp Pro Tyr Tyr Gly Arg
        115                 120                 125

Gly Pro Ile Gln Leu Thr His Glu Tyr Asn Tyr Arg Leu Ala Gly Gln
    130                 135                 140

Ala Leu Asn Leu Asn Leu Val Gly Asn Pro Asp Leu Val Ala Ser Asp
145                 150                 155                 160

Pro Val Val Ala Phe Lys Thr Ala Ile Trp Phe Trp Met Thr Pro Gln
                165                 170                 175

Ser Pro Lys Pro Ser Cys His Ala Val Met Thr Gly Ala Trp Thr Pro
            180                 185                 190

Ser Ala Thr Asp Arg Ala Ala Gly Arg Leu Pro Gly Tyr Gly Leu Thr
        195                 200                 205

Ser Asn Ile Ile Asn Gly Gly Leu Glu Cys Gly Lys Gly Gln Ser Thr
    210                 215                 220

Asp Gly Ala Lys Asp Arg Val Gly Tyr Tyr Lys Arg Tyr Cys Asp Met
```

```
                    225                 230                 235                 240
Leu Arg Val Gly Tyr Gly Asp Asn Val Pro Cys Lys Asp Gln Lys Pro
                    245                 250                 255

Tyr Gly Gly

<210> SEQ ID NO 19
<211> LENGTH: 1013
<212> TYPE: DNA
<213> ORGANISM: Zea mays
<220> FEATURE:
<221> NAME/KEY: CDS
<222> LOCATION: (75)...(830)

<400> SEQUENCE: 19
agacagctag cccacatagc ccttccagca acgcgcgatc gaagggttga gagctattgg      60
aagcaagtac gtgc atg gcg agg ttt gcg ctc gtg gcg tgc gcc gct gcc      110
             Met Ala Arg Phe Ala Leu Val Ala Cys Ala Ala Ala
               1               5                  10 acg gcg gcg ctg ctg ctc ggc gtg gcg gca gcg gac gtg gcg tcg atc      158
Thr Ala Ala Leu Leu Leu Gly Val Ala Ala Ala Asp Val Ala Ser Ile
         15                  20                  25 atc acg cag gac gtg tac aac cag atg ctg ccc aac cgc gac aac acg      206
Ile Thr Gln Asp Val Tyr Asn Gln Met Leu Pro Asn Arg Asp Asn Thr
     30                  35                  40 cag tgc ccc gcc aac ggc ttc tac acc tac gac gcc ttc atc cag gcc      254
Gln Cys Pro Ala Asn Gly Phe Tyr Thr Tyr Asp Ala Phe Ile Gln Ala
 45                  50                  55                  60 gtc aac ttc ttc ccg ggg ttc ggc acc ggc tcc agc acc gac gaa ctc      302
Val Asn Phe Phe Pro Gly Phe Gly Thr Gly Ser Ser Thr Asp Glu Leu
                 65                  70                  75 aac aag cgc gag ctc gcc gcc ttc ttc ggc cag acc tcc cac gag act      350
Asn Lys Arg Glu Leu Ala Ala Phe Phe Gly Gln Thr Ser His Glu Thr
             80                  85                  90 acc ggt ggc acg aca ggt gcc gcc gac cag ttc cag tgg ggt tac tgc      398
Thr Gly Gly Thr Thr Gly Ala Ala Asp Gln Phe Gln Trp Gly Tyr Cys
         95                 100                 105 ttc aag gag gag atc aac aag gcc aca agt cct ccc tac tat gga cgc      446
Phe Lys Glu Glu Ile Asn Lys Ala Thr Ser Pro Pro Tyr Tyr Gly Arg
    110                 115                 120 gga cca att caa ttg aca ggg cag gcc aac tac cag caa gcc ggg gac      494
Gly Pro Ile Gln Leu Thr Gly Gln Ala Asn Tyr Gln Gln Ala Gly Asp
125                 130                 135                 140 gcg ata ggc gag gac ctg gtg aac aac ccg gac ctg gtg tcc tcg gac      542
Ala Ile Gly Glu Asp Leu Val Asn Asn Pro Asp Leu Val Ser Ser Asp
                145                 150                 155 gcg gtg gtc tcc ttc aag acg gcc atc tgg ttc tgg atg acg gcg cag      590
Ala Val Val Ser Phe Lys Thr Ala Ile Trp Phe Trp Met Thr Ala Gln
            160                 165                 170 tcg ccc aag ccg tcg tgc cac gac gtg atc ctc ggc aac tgg acg ccg      638
Ser Pro Lys Pro Ser Cys His Asp Val Ile Leu Gly Asn Trp Thr Pro
        175                 180                 185 tcg agc gcc gac gcg gcg gcg ggg cgg gtt ccc ggc tac ggc gcc atc      686
Ser Ser Ala Asp Ala Ala Ala Gly Arg Val Pro Gly Tyr Gly Ala Ile
    190                 195                 200 acc aac atc atc aac ggc gcc aaa gac tgc ggc gtg ggg caa aac gcc      734
Thr Asn Ile Ile Asn Gly Ala Lys Asp Cys Gly Val Gly Gln Asn Ala
205                 210                 215                 220 gcc aac gtc gac cgc atc ggc tac tac aag cgc tac tgc gac atg ctc      782
Ala Asn Val Asp Arg Ile Gly Tyr Tyr Lys Arg Tyr Cys Asp Met Leu
                225                 230                 235
```

-continued

```
ggc gtc ggc tac ggc gac aac ctc gac tgc tac tcc cag cag cac ttc    830
Gly Val Gly Tyr Gly Asp Asn Leu Asp Cys Tyr Ser Gln Gln His Phe
            240                 245                 250 tgatgaactg ctgttcgact tgactgctag cactgttgct acagtataag atctgtgtcc   890
ggacgtgttc catacatatt ttattatttt aatacaataa aggctgatga tccggttata   950
tatatatgaa atctttatct tattatgaac atgggatttt cgaactccaa aaaaaaaaaa  1010
aaa                                                                1013
```

<210> SEQ ID NO 20
<211> LENGTH: 252
<212> TYPE: PRT
<213> ORGANISM: Zea mays

<400> SEQUENCE: 20

```
Met Ala Arg Phe Ala Leu Val Ala Cys Ala Ala Thr Ala Ala Leu
 1               5                  10                  15

Leu Leu Gly Val Ala Ala Asp Val Ala Ser Ile Ile Thr Gln Asp
             20                  25                  30

Val Tyr Asn Gln Met Leu Pro Asn Arg Asp Asn Thr Gln Cys Pro Ala
         35                  40                  45

Asn Gly Phe Tyr Thr Tyr Asp Ala Phe Ile Gln Ala Val Asn Phe Phe
     50                  55                  60

Pro Gly Phe Gly Thr Gly Ser Ser Thr Asp Glu Leu Asn Lys Arg Glu
65                  70                  75                  80

Leu Ala Ala Phe Phe Gly Gln Thr Ser His Glu Thr Thr Gly Gly Thr
                 85                  90                  95

Thr Gly Ala Ala Asp Gln Phe Gln Trp Gly Tyr Cys Phe Lys Glu Glu
            100                 105                 110

Ile Asn Lys Ala Thr Ser Pro Pro Tyr Tyr Gly Arg Gly Pro Ile Gln
        115                 120                 125

Leu Thr Gly Gln Ala Asn Tyr Gln Gln Ala Gly Asp Ala Ile Gly Glu
    130                 135                 140

Asp Leu Val Asn Asn Pro Asp Leu Val Ser Ser Asp Ala Val Val Ser
145                 150                 155                 160

Phe Lys Thr Ala Ile Trp Phe Trp Met Thr Ala Gln Ser Pro Lys Pro
                165                 170                 175

Ser Cys His Asp Val Ile Leu Gly Asn Trp Thr Pro Ser Ser Ala Asp
            180                 185                 190

Ala Ala Ala Gly Arg Val Pro Gly Tyr Gly Ala Ile Thr Asn Ile Ile
        195                 200                 205

Asn Gly Ala Lys Asp Cys Gly Val Gly Gln Asn Ala Ala Asn Val Asp
    210                 215                 220

Arg Ile Gly Tyr Tyr Lys Arg Tyr Cys Asp Met Leu Gly Val Gly Tyr
225                 230                 235                 240

Gly Asp Asn Leu Asp Cys Tyr Ser Gln Gln His Phe
                245                 250
```

<210> SEQ ID NO 21
<211> LENGTH: 1048
<212> TYPE: DNA
<213> ORGANISM: Zea mays
<220> FEATURE:
<221> NAME/KEY: CDS
<222> LOCATION: (42)...(854)

<400> SEQUENCE: 21

```
ccgggcatcg cgggcatcgc acacaaacgc aacctgcagc c atg gca cag aag ctc      56
                                              Met Ala Gln Lys Leu
                                                1               5 gcg cca ccg acg gcg gcg gtc gtc gtc ctg ctg gcg ctc gcc ttg            104
Ala Pro Pro Thr Ala Ala Val Val Val Leu Leu Ala Leu Ala Leu
            10              15                  20 tcg gcc gcc gcg cag aac tgc ggg tgc gcg tcg ggc ctg tgc tgc agc        152
Ser Ala Ala Ala Gln Asn Cys Gly Cys Ala Ser Gly Leu Cys Cys Ser
                25                  30                  35 cgg ttc ggg tac tgc ggg acg ggc gag gac tac tgc ggc gcc ggg tgc        200
Arg Phe Gly Tyr Cys Gly Thr Gly Glu Asp Tyr Cys Gly Ala Gly Cys
        40                  45                  50 cag tcg ggc ccc tgc gac gtg ccg gag acc aac aac gcg tcc gtg gcc        248
Gln Ser Gly Pro Cys Asp Val Pro Glu Thr Asn Asn Ala Ser Val Ala
 55                  60                  65 agc atc gtg acg ccg gcc ttc ttc gac gcg ctc ctc gcg cag gcc gcc        296
Ser Ile Val Thr Pro Ala Phe Phe Asp Ala Leu Leu Ala Gln Ala Ala
         70                  75                  80              85 gcc tcg tgc gag gcc aac ggc ttc tac acc cgc gac gcc ttc ctc gcc        344
Ala Ser Cys Glu Ala Asn Gly Phe Tyr Thr Arg Asp Ala Phe Leu Ala
                 90                  95                 100 gcc gcc ggc tac tac ccg gcg ttc ggc cgc acc ggc acc gtc gac gac        392
Ala Ala Gly Tyr Tyr Pro Ala Phe Gly Arg Thr Gly Thr Val Asp Asp
             105                 110                 115 tcc aag cgc gag atc gcc gcc ttc ttc ggc aac gcc aac cac gag acc        440
Ser Lys Arg Glu Ile Ala Ala Phe Phe Gly Asn Ala Asn His Glu Thr
        120                 125                 130 ata aag ttc tgc tac atc aac gag atc gac ggg ccg agc aag aac tac        488
Ile Lys Phe Cys Tyr Ile Asn Glu Ile Asp Gly Pro Ser Lys Asn Tyr
    135                 140                 145 tgc gac cgg aac aac acg cag tgg ccg tgc cag gcg ggg aag ggg tac        536
Cys Asp Arg Asn Asn Thr Gln Trp Pro Cys Gln Ala Gly Lys Gly Tyr
150                 155                 160                 165 tac ggc cgc ggc ccg ctg cag atc tcc tgg aac ttc aac tac ggg ccc        584
Tyr Gly Arg Gly Pro Leu Gln Ile Ser Trp Asn Phe Asn Tyr Gly Pro
                170                 175                 180 gcg ggg cag agc atc ggc ttc gac ggg ctg ggc gac ccc gac gcg gtg        632
Ala Gly Gln Ser Ile Gly Phe Asp Gly Leu Gly Asp Pro Asp Ala Val
            185                 190                 195 gcg cgc agc gcc gtg ctc gcg ttc cgc tcc gcg ctc tgg tac tgg atg        680
Ala Arg Ser Ala Val Leu Ala Phe Arg Ser Ala Leu Trp Tyr Trp Met
        200                 205                 210 aac aac gtg cac ggg gcc atc gtc tcc ggc cag ggc ttc ggc gcc acc        728
Asn Asn Val His Gly Ala Ile Val Ser Gly Gln Gly Phe Gly Ala Thr
    215                 220                 225 atc cgg gcc atc aac ggc gcg ctc gag tgc gac ggc aag aac ccc aac        776
Ile Arg Ala Ile Asn Gly Ala Leu Glu Cys Asp Gly Lys Asn Pro Asn
230                 235                 240                 245 tcc gtc aac aac cgc gtc gcc tac tac aag cag ttc tgc cag gat ttc        824
Ser Val Asn Asn Arg Val Ala Tyr Tyr Lys Gln Phe Cys Gln Asp Phe
                250                 255                 260 ggc gtc gac ccg ggc aac aac ctc acc tgc tgaatgatct ctctctcatt         874
Gly Val Asp Pro Gly Asn Asn Leu Thr Cys
            265                 270 gggttgttgt cctgtactta cacatgtgtt ggttgatgga tagatggcga ttgcgtggtg     934
cggatgtttc ggtttggcgg tgtcaattct gatatgcgcg tcgtgctgt tctgatactg      994 actatatacg gaaataaaaa tctgatttgc attaaaaaaa aaaaaaaaaa aaaa          1048
```

<210> SEQ ID NO 22
<211> LENGTH: 271
<212> TYPE: PRT
<213> ORGANISM: Zea mays

<400> SEQUENCE: 22

```
Met Ala Gln Lys Leu Ala Pro Pro Thr Ala Ala Val Val Val Leu
 1               5                  10                  15

Leu Ala Leu Ala Leu Ser Ala Ala Gln Asn Cys Gly Cys Ala Ser
                 20                  25                  30

Gly Leu Cys Cys Ser Arg Phe Gly Tyr Cys Gly Thr Gly Glu Asp Tyr
             35                  40                  45

Cys Gly Ala Gly Cys Gln Ser Gly Pro Cys Asp Val Pro Glu Thr Asn
 50                  55                  60

Asn Ala Ser Val Ala Ser Ile Val Thr Pro Ala Phe Phe Asp Ala Leu
 65                  70                  75                  80

Leu Ala Gln Ala Ala Ser Cys Glu Ala Asn Gly Phe Tyr Thr Arg
                 85                  90                  95

Asp Ala Phe Leu Ala Ala Gly Tyr Tyr Pro Ala Phe Gly Arg Thr
                100                 105                 110

Gly Thr Val Asp Asp Ser Lys Arg Glu Ile Ala Ala Phe Phe Gly Asn
                115                 120                 125

Ala Asn His Glu Thr Ile Lys Phe Cys Tyr Ile Asn Glu Ile Asp Gly
 130                 135                 140

Pro Ser Lys Asn Tyr Cys Asp Arg Asn Asn Thr Gln Trp Pro Cys Gln
 145                 150                 155                 160

Ala Gly Lys Gly Tyr Tyr Gly Arg Gly Pro Leu Gln Ile Ser Trp Asn
                 165                 170                 175

Phe Asn Tyr Gly Pro Ala Gly Gln Ser Ile Gly Phe Asp Gly Leu Gly
                 180                 185                 190

Asp Pro Asp Ala Val Ala Arg Ser Ala Val Leu Ala Phe Arg Ser Ala
                 195                 200                 205

Leu Trp Tyr Trp Met Asn Asn Val His Gly Ala Ile Val Ser Gly Gln
 210                 215                 220

Gly Phe Gly Ala Thr Ile Arg Ala Ile Asn Gly Ala Leu Glu Cys Asp
225                  230                 235                 240

Gly Lys Asn Pro Asn Ser Val Asn Asn Arg Val Ala Tyr Tyr Lys Gln
                 245                 250                 255

Phe Cys Gln Asp Phe Gly Val Asp Pro Gly Asn Asn Leu Thr Cys
                 260                 265                 270
```

<210> SEQ ID NO 23
<211> LENGTH: 1118
<212> TYPE: DNA
<213> ORGANISM: Zea mays
<220> FEATURE:
<221> NAME/KEY: CDS
<222> LOCATION: (90)...(941)

<400> SEQUENCE: 23

```
ccgtaatcca aggggaaccc gacgcacaga tcacttgtgg caggcacccg gccgtgactt      60
gatcgcaatc acaaccatca tcatcgaca atg gcg gcg tat tct tgc gcc ttg       113
                                Met Ala Ala Tyr Ser Cys Ala Leu
                                  1               5 tgg act gct gct tcc gtg gtc gct ttc ctt gtc atc ggc gta gca gag       161
Trp Thr Ala Ala Ser Val Val Ala Phe Leu Val Ile Gly Val Ala Glu
        10                  15                  20
```

```
gcg agg tac ggc ggc cct ggg cag tgg agg agg cct gcc cct gcc cct       209
Ala Arg Tyr Gly Gly Pro Gly Gln Trp Arg Arg Pro Ala Pro Ala Pro
 25                  30                  35                  40 gtt gtc cct gtg gcg gcc ctc gtc agc gag cag ctg tac ggc tcc ctg       257
Val Val Pro Val Ala Ala Leu Val Ser Glu Gln Leu Tyr Gly Ser Leu
                 45                  50                  55 ttc ctg cac aag gac gac gac gcc tgc ccc gcc aag ggc ttc tac acc       305
Phe Leu His Lys Asp Asp Asp Ala Cys Pro Ala Lys Gly Phe Tyr Thr
             60                  65                  70 tat gcc tcc ttc atc cag gcc gcc agg acg ttc ccc acg ttc gcc gcc       353
Tyr Ala Ser Phe Ile Gln Ala Ala Arg Thr Phe Pro Thr Phe Ala Ala
         75                  80                  85 act ggc gac ctc agc acc cgc aaa cgc gag gtc gcg gcc ttc ctc gcg       401
Thr Gly Asp Leu Ser Thr Arg Lys Arg Glu Val Ala Ala Phe Leu Ala
     90                  95                 100 caa atc tct cac gag acc aca ggc ggg tgg gcg acg gcg ccg gac ggc       449
Gln Ile Ser His Glu Thr Thr Gly Gly Trp Ala Thr Ala Pro Asp Gly
105                 110                 115                 120 agt acg tgg ggc ctg tgc tac aag gag gag atc aag ccg gcg agc aac       497
Ser Thr Trp Gly Leu Cys Tyr Lys Glu Glu Ile Lys Pro Ala Ser Asn
                125                 130                 135 tac tgc gac gcg acg gac gag cag tgg ccg tgc tac ccg ggc aag tcc       545
Tyr Cys Asp Ala Thr Asp Glu Gln Trp Pro Cys Tyr Pro Gly Lys Ser
            140                 145                 150 tac cac ggt cgg ggc ccc atc cag ctc tcc tgg aac ttc aac tac ggg       593
Tyr His Gly Arg Gly Pro Ile Gln Leu Ser Trp Asn Phe Asn Tyr Gly
        155                 160                 165 ccg gcg ggc cag gcg ctg ggc ttc gac ggc ctg cgc aac ccg gag ctg       641
Pro Ala Gly Gln Ala Leu Gly Phe Asp Gly Leu Arg Asn Pro Glu Leu
    170                 175                 180 gtg gcc aac tgc tcc cag acc gcg ttc cgg acg gcg ctc tgg ttc tgg       689
Val Ala Asn Cys Ser Gln Thr Ala Phe Arg Thr Ala Leu Trp Phe Trp
185                 190                 195                 200 atg acg ccg cgc cgc ccc aag ccg tcg tgc cac gag gtc atg gtc gga       737
Met Thr Pro Arg Arg Pro Lys Pro Ser Cys His Glu Val Met Val Gly
                205                 210                 215 gag tac cgc ccc acg ccc gcc gac gcc gcg gcc aac cgg acg ccc ggc       785
Glu Tyr Arg Pro Thr Pro Ala Asp Ala Ala Ala Asn Arg Thr Pro Gly
            220                 225                 230 ttt ggc ctc gtc acc aac atc gtc aac ggc ggc ctc gag tgc aac cgc       833
Phe Gly Leu Val Thr Asn Ile Val Asn Gly Gly Leu Glu Cys Asn Arg
        235                 240                 245 acc gac gat gcc cgg gtc aac aac cgg att ggc ttc tac cag agg tac       881
Thr Asp Asp Ala Arg Val Asn Asn Arg Ile Gly Phe Tyr Gln Arg Tyr
    250                 255                 260 tgc cat atc ttc aac gtt gac gcc ggc ccc aac ctc gac tgc gca cac       929
Cys His Ile Phe Asn Val Asp Ala Gly Pro Asn Leu Asp Cys Ala His
265                 270                 275                 280 cag cag ccc tac tagtgtagtg tctacggggt tacgttctaa gctgtttgcc           981
Gln Gln Pro Tyr tgtttctaac agagttgatg atagcgtttt ggatgatcgt tctcttgttc tgacctatac    1041
aaaacacagt atatatatca ataaaaaaca gtagacgact gtgactctct gagctaaaaa    1101
aaaaaaaaaa aaaaaaa                                                   1118

<210> SEQ ID NO 24
<211> LENGTH: 284
<212> TYPE: PRT
```

<213> ORGANISM: Zea mays

<400> SEQUENCE: 24

Met Ala Ala Tyr Ser Cys Ala Leu Trp Thr Ala Ala Ser Val Val Ala
1               5                   10                  15

Phe Leu Val Ile Gly Val Ala Glu Ala Arg Tyr Gly Gly Pro Gly Gln
            20                  25                  30

Trp Arg Arg Pro Ala Pro Ala Pro Val Val Pro Val Ala Ala Leu Val
        35                  40                  45

Ser Glu Gln Leu Tyr Gly Ser Leu Phe Leu His Lys Asp Asp Asp Ala
    50                  55                  60

Cys Pro Ala Lys Gly Phe Tyr Thr Tyr Ala Ser Phe Ile Gln Ala Ala
65                  70                  75                  80

Arg Thr Phe Pro Thr Phe Ala Ala Thr Gly Asp Leu Ser Thr Arg Lys
                85                  90                  95

Arg Glu Val Ala Ala Phe Leu Ala Gln Ile Ser His Glu Thr Thr Gly
            100                 105                 110

Gly Trp Ala Thr Ala Pro Asp Gly Ser Thr Trp Gly Leu Cys Tyr Lys
        115                 120                 125

Glu Glu Ile Lys Pro Ala Ser Asn Tyr Cys Asp Ala Thr Asp Glu Gln
130                 135                 140

Trp Pro Cys Tyr Pro Gly Lys Ser Tyr His Gly Arg Gly Pro Ile Gln
145                 150                 155                 160

Leu Ser Trp Asn Phe Asn Tyr Gly Pro Ala Gly Gln Ala Leu Gly Phe
                165                 170                 175

Asp Gly Leu Arg Asn Pro Glu Leu Val Ala Asn Cys Ser Gln Thr Ala
            180                 185                 190

Phe Arg Thr Ala Leu Trp Phe Trp Met Thr Pro Arg Arg Pro Lys Pro
        195                 200                 205

Ser Cys His Glu Val Met Val Gly Glu Tyr Arg Pro Thr Pro Ala Asp
    210                 215                 220

Ala Ala Ala Asn Arg Thr Pro Gly Phe Gly Leu Val Thr Asn Ile Val
225                 230                 235                 240

Asn Gly Gly Leu Glu Cys Asn Arg Thr Asp Asp Ala Arg Val Asn Asn
                245                 250                 255

Arg Ile Gly Phe Tyr Gln Arg Tyr Cys His Ile Phe Asn Val Asp Ala
            260                 265                 270

Gly Pro Asn Leu Asp Cys Ala His Gln Gln Pro Tyr
        275                 280

<210> SEQ ID NO 25
<211> LENGTH: 583
<212> TYPE: DNA
<213> ORGANISM: Zea mays
<220> FEATURE:
<221> NAME/KEY: CDS
<222> LOCATION: (2)...(466)

<400> SEQUENCE: 25 g cgg ccg cag tgg ccg tgc gcg ccc ggc aag aag tac ttc ggc cgc ggc    49
  Arg Pro Gln Trp Pro Cys Ala Pro Gly Lys Lys Tyr Phe Gly Arg Gly
  1               5                   10                  15 ccc atc cag atc tcc ttc aac tac aac tac ggc ccg gcg ggg cga gcc    97
Pro Ile Gln Ile Ser Phe Asn Tyr Asn Tyr Gly Pro Ala Gly Arg Ala
            20                  25                  30 atc ggc gtg gac ctc ctc aac aac ccg gac ctc gtc gcg acg gac ccc    145
Ile Gly Val Asp Leu Leu Asn Asn Pro Asp Leu Val Ala Thr Asp Pro

```
                35                  40                  45
gtg ata tcc ttc aag aca gcg ctg tgg ttc tgg atg aac gcg cgg gac    193
Val Ile Ser Phe Lys Thr Ala Leu Trp Phe Trp Met Asn Ala Arg Asp
     50                  55                  60 aac aag ccg tcg tgc cac gcc gtg atc acg ggg cag tgg acg ccc acg    241
Asn Lys Pro Ser Cys His Ala Val Ile Thr Gly Gln Trp Thr Pro Thr
 65                  70                  75                  80 gct gcg gac agg gcg gcc ggc cgg ggc gcg cca ggg tac ggc gtg atc    289
Ala Ala Asp Arg Ala Ala Gly Arg Gly Ala Pro Gly Tyr Gly Val Ile
                 85                  90                  95 acc aac atc atc aac ggt ggg atc gag tgc ggg cac ggg acg gac ccc    337
Thr Asn Ile Ile Asn Gly Gly Ile Glu Cys Gly His Gly Thr Asp Pro
            100                 105                 110 cgg gtc acc gac cgg att ggc ttc tac aag cgc tac tgc gat gtc ttc    385
Arg Val Thr Asp Arg Ile Gly Phe Tyr Lys Arg Tyr Cys Asp Val Phe
        115                 120                 125 cgc atc ggc tac ggg agc aat ctc gat tgc gac ggc cag agg ccc ttc    433
Arg Ile Gly Tyr Gly Ser Asn Leu Asp Cys Asp Gly Gln Arg Pro Phe
    130                 135                 140 aat agc gga ctg gcg gtt gag gtg gcg gcg cag tgaaaacgtg tgtgtgtg    486
Asn Ser Gly Leu Ala Val Glu Val Ala Ala Gln
145                 150                 155 tgtgactgtg tgttgcttcg tcggtttgaa taaatttcat gtaaaaaccg gtgcttcatc   546
cgaaaataag gcactttact taaaaaaaaa aaaaaaa                            583

<210> SEQ ID NO 26
<211> LENGTH: 155
<212> TYPE: PRT
<213> ORGANISM: Zea mays

<400> SEQUENCE: 26

Arg Pro Gln Trp Pro Cys Ala Pro Gly Lys Lys Tyr Phe Gly Arg Gly
  1               5                  10                  15

Pro Ile Gln Ile Ser Phe Asn Tyr Asn Tyr Gly Pro Ala Gly Arg Ala
             20                  25                  30

Ile Gly Val Asp Leu Leu Asn Asn Pro Asp Leu Val Ala Thr Asp Pro
         35                  40                  45

Val Ile Ser Phe Lys Thr Ala Leu Trp Phe Trp Met Asn Ala Arg Asp
     50                  55                  60

Asn Lys Pro Ser Cys His Ala Val Ile Thr Gly Gln Trp Thr Pro Thr
 65                  70                  75                  80

Ala Ala Asp Arg Ala Ala Gly Arg Gly Ala Pro Gly Tyr Gly Val Ile
                 85                  90                  95

Thr Asn Ile Ile Asn Gly Gly Ile Glu Cys Gly His Gly Thr Asp Pro
            100                 105                 110

Arg Val Thr Asp Arg Ile Gly Phe Tyr Lys Arg Tyr Cys Asp Val Phe
        115                 120                 125

Arg Ile Gly Tyr Gly Ser Asn Leu Asp Cys Asp Gly Gln Arg Pro Phe
    130                 135                 140

Asn Ser Gly Leu Ala Val Glu Val Ala Ala Gln
145                 150                 155

<210> SEQ ID NO 27
<211> LENGTH: 655
<212> TYPE: DNA
<213> ORGANISM: Zea mays
<220> FEATURE:
<221> NAME/KEY: CDS
```

```
<222> LOCATION: (2)...(523)
<221> NAME/KEY: misc_feature
<222> LOCATION: (1)...(655)
<223> OTHER INFORMATION: n = A,T,C or G

<400> SEQUENCE: 27 c cca cgc gtc cgg tgg aac aat ttc ttg gga ggt cag tca tct tcc cgc      49
  Pro Arg Val Arg Trp Asn Asn Phe Leu Gly Gly Gln Ser Ser Ser Arg
   1               5                  10                  15 ccc ttg ggt gat gcg atc ctt gat ggc ata gac ttc gac att gag ggc        97
Pro Leu Gly Asp Ala Ile Leu Asp Gly Ile Asp Phe Asp Ile Glu Gly
                 20                  25                  30 ggc aca aac cag cac tgg gat gat ctt gcg aga tac ctg aaa ggg tac       145
Gly Thr Asn Gln His Trp Asp Asp Leu Ala Arg Tyr Leu Lys Gly Tyr
             35                  40                  45 agc aac tct ggc agg agg gtg tac ctg acc gct gcg cct caa tgc ccg       193
Ser Asn Ser Gly Arg Arg Val Tyr Leu Thr Ala Ala Pro Gln Cys Pro
 50                  55                  60 ttt cct gat agc tgg gtc ggt ggc gcg ctc aac acc ggc ctg ttt gac       241
Phe Pro Asp Ser Trp Val Gly Gly Ala Leu Asn Thr Gly Leu Phe Asp
 65                  70                  75                  80 tac gtc tgg gtg cag ttc tac aac aac cct cct tgc cag tac agc tca       289
Tyr Val Trp Val Gln Phe Tyr Asn Asn Pro Pro Cys Gln Tyr Ser Ser
                 85                  90                  95 ggc agc acc act gat ctt gct gat gca tgg aag cag tgg ctg tca att       337
Gly Ser Thr Thr Asp Leu Ala Asp Ala Trp Lys Gln Trp Leu Ser Ile
             100                 105                 110 ccg gcg aag cag atc ttt ctt gga ctc ccg gct tcc cct caa gca gct       385
Pro Ala Lys Gln Ile Phe Leu Gly Leu Pro Ala Ser Pro Gln Ala Ala
         115                 120                 125 ggg agt ggg ttt ata cca act gat gac ctc aag tct caa gtg ctt ccg       433
Gly Ser Gly Phe Ile Pro Thr Asp Asp Leu Lys Ser Gln Val Leu Pro
 130                 135                 140 ttg atc aag agc tca agg aaa tat gga ggg atc atg ctg tgg tcc aag       481
Leu Ile Lys Ser Ser Arg Lys Tyr Gly Gly Ile Met Leu Trp Ser Lys
145                 150                 155                 160 tac tat gat gac caa gat ggc tac agt tct tca gtg aaa aag                523
Tyr Tyr Asp Asp Gln Asp Gly Tyr Ser Ser Ser Val Lys Lys
                 165                 170 tgatgtgtaa gttgtttgcg tgtggtgtgc cacaatatcc tgtgtgttac ntgtgtgtat     583
gtgaaaaaac tatgtgttga ctctgttaag gaaaataaac gtgcaatggt ccnggtgtgt     643
antaattaag ga                                                          655

<210> SEQ ID NO 28
<211> LENGTH: 174
<212> TYPE: PRT
<213> ORGANISM: Zea mays

<400> SEQUENCE: 28

Pro Arg Val Arg Trp Asn Asn Phe Leu Gly Gly Gln Ser Ser Ser Arg
 1               5                  10                  15

Pro Leu Gly Asp Ala Ile Leu Asp Gly Ile Asp Phe Asp Ile Glu Gly
                 20                  25                  30

Gly Thr Asn Gln His Trp Asp Asp Leu Ala Arg Tyr Leu Lys Gly Tyr
             35                  40                  45

Ser Asn Ser Gly Arg Arg Val Tyr Leu Thr Ala Ala Pro Gln Cys Pro
 50                  55                  60

Phe Pro Asp Ser Trp Val Gly Gly Ala Leu Asn Thr Gly Leu Phe Asp
65                  70                  75                  80
```

-continued

```
Tyr Val Trp Val Gln Phe Tyr Asn Asn Pro Pro Cys Gln Tyr Ser Ser
                85                  90                  95
Gly Ser Thr Thr Asp Leu Ala Asp Ala Trp Lys Gln Trp Leu Ser Ile
            100                 105                 110
Pro Ala Lys Gln Ile Phe Leu Gly Leu Pro Ala Ser Pro Gln Ala Ala
            115                 120                 125
Gly Ser Gly Phe Ile Pro Thr Asp Leu Lys Ser Gln Val Leu Pro
130                 135                 140
Leu Ile Lys Ser Ser Arg Lys Tyr Gly Ile Met Leu Trp Ser Lys
145                 150                 155                 160
Tyr Tyr Asp Asp Gln Asp Gly Tyr Ser Ser Val Lys Lys
                165                 170
```

<210> SEQ ID NO 29
<211> LENGTH: 881
<212> TYPE: DNA
<213> ORGANISM: Zea mays
<220> FEATURE:
<221> NAME/KEY: CDS
<222> LOCATION: (3)...(551)

<400> SEQUENCE: 29

```
at gcc ggg agc tgg tgc gag ggc aga cgc ttc tac acg cga agc gcg       47
   Ala Gly Ser Trp Cys Glu Gly Arg Arg Phe Tyr Thr Arg Ser Ala
   1               5                   10                  15 ttc ctc gag gcc atc gcc gcg tac ccg ggc ttc gcg cat ggc ggc tcc      95
Phe Leu Glu Ala Ile Ala Ala Tyr Pro Gly Phe Ala His Gly Gly Ser
                20                  25                  30 gag gtc gag cgc aag cgc gag att gcc gcc ttc ttc gcg cat gtc acg     143
Glu Val Glu Arg Lys Arg Glu Ile Ala Ala Phe Phe Ala His Val Thr
            35                  40                  45 cac gag acc ggg cat ttg tgc tac atc aac gag gtc gac gtg gcg aag     191
His Glu Thr Gly His Leu Cys Tyr Ile Asn Glu Val Asp Val Ala Lys
        50                  55                  60 tac tgc gac tgg agc agt gag aag cag tgg ccg tgc cac ccc agg cag     239
Tyr Cys Asp Trp Ser Ser Glu Lys Gln Trp Pro Cys His Pro Arg Gln
65                  70                  75 ggt tac tac ggg cgc ggc ccg ctg cag ctg tcg tgg aac tac aac tac     287
Gly Tyr Tyr Gly Arg Gly Pro Leu Gln Leu Ser Trp Asn Tyr Asn Tyr
80                  85                  90                  95 ggg ccg gcg ggg agg agc ctc ggc ttc gac ggg ctg gga gac ccg gac     335
Gly Pro Ala Gly Arg Ser Leu Gly Phe Asp Gly Leu Gly Asp Pro Asp
                100                 105                 110 aga ctg gcg cag gac ccc gtg ttg tcg ttc aag tcg gcg ctc tgg tac     383
Arg Leu Ala Gln Asp Pro Val Leu Ser Phe Lys Ser Ala Leu Trp Tyr
            115                 120                 125 tgg atg gag aac atg cac cag ctc atg ccc cag ggg ttc ggc gcc acc     431
Trp Met Glu Asn Met His Gln Leu Met Pro Gln Gly Phe Gly Ala Thr
        130                 135                 140 atc agg gcc atc aac ggc ttc gac gag tgt cac ggc ggg aag aac acg     479
Ile Arg Ala Ile Asn Gly Phe Asp Glu Cys His Gly Gly Lys Asn Thr
145                 150                 155 gcc gaa atg aaa gac cgg gtg cgc ttc tac ctc gag tac tgc cac cac     527
Ala Glu Met Lys Asp Arg Val Arg Phe Tyr Leu Glu Tyr Cys His His
160                 165                 170                 175 ttc cgt gtt cac ccc ggg ctc gac ctcagttgct agatacgtac gtgctcagtc     581
Phe Arg Val His Pro Gly Leu Asp
                180 tttcatcgat attgtgagct tgttggatta gtgcatcttt cagtgttaga gctcatccag    641
```

```
atgctgctaa gcgtcttgtc tcttgtctct ctgtccagcc tgacgtccag ctgcgttatc    701
ggcagtcaag tctttcctgt tttgttggag aagatcgcgc tccatgatct gtttgcgcct    761
ttgtgggatg ccacgaatcg gagtcatgac cagtagatgt tgtgaggct gattttggtg    821 gcattttcag taatctctcc tactctataa agctgtacca tgaaaaaaaa aaaaaaaaa    881
```

```
<210> SEQ ID NO 30
<211> LENGTH: 183
<212> TYPE: PRT
<213> ORGANISM: Zea mays

<400> SEQUENCE: 30
```

```
Ala Gly Ser Trp Cys Glu Gly Arg Arg Phe Tyr Thr Arg Ser Ala Phe
 1               5                  10                  15

Leu Glu Ala Ile Ala Ala Tyr Pro Gly Phe Ala His Gly Gly Ser Glu
            20                  25                  30

Val Glu Arg Lys Arg Glu Ile Ala Ala Phe Phe Ala His Val Thr His
        35                  40                  45

Glu Thr Gly His Leu Cys Tyr Ile Asn Glu Val Asp Val Ala Lys Tyr
 50                  55                  60

Cys Asp Trp Ser Ser Glu Lys Gln Trp Pro Cys His Pro Arg Gln Gly
65                   70                  75                   80

Tyr Tyr Gly Arg Gly Pro Leu Gln Leu Ser Trp Asn Tyr Asn Tyr Gly
                85                  90                  95

Pro Ala Gly Arg Ser Leu Gly Phe Asp Gly Leu Gly Asp Pro Asp Arg
            100                 105                 110

Leu Ala Gln Asp Pro Val Leu Ser Phe Lys Ser Ala Leu Trp Tyr Trp
        115                 120                 125

Met Glu Asn Met His Gln Leu Met Pro Gln Gly Phe Gly Ala Thr Ile
130                 135                 140

Arg Ala Ile Asn Gly Phe Asp Glu Cys His Gly Gly Lys Asn Thr Ala
145                 150                 155                 160

Glu Met Lys Asp Arg Val Arg Phe Tyr Leu Glu Tyr Cys His His Phe
                165                 170                 175

Arg Val His Pro Gly Leu Asp
            180
```

```
<210> SEQ ID NO 31
<211> LENGTH: 1116
<212> TYPE: DNA
<213> ORGANISM: Zea mays
<220> FEATURE:
<221> NAME/KEY: intron
<222> LOCATION: (445)...(512)
<221> NAME/KEY: CDS
<222> LOCATION: (42)...(444)
<221> NAME/KEY: CDS
<222> LOCATION: (513)...(922)

<400> SEQUENCE: 31
```

```
ccgggcatcg cgggcatcgc acacaaacgc aacctgcagc c atg gca cag aag ctc    56
                                             Met Ala Gln Lys Leu
                                              1               5 gcg cca ccg acg gcg gcg gtc gtc gtc gtc ctg ctg gcg ctc gcc ttg       104
Ala Pro Pro Thr Ala Ala Val Val Val Val Leu Leu Ala Leu Ala Leu
            10                  15                  20 tcg gcc gcc gcg cag aac tgc ggg tgc gcg tcg ggc ctg tgc tgc agc       152
Ser Ala Ala Ala Gln Asn Cys Gly Cys Ala Ser Gly Leu Cys Cys Ser
        25                  30                  35
```

```
cgg ttc ggg tac tgc ggg acg ggc gag gac tac tgc ggc gcc ggg tgc      200
Arg Phe Gly Tyr Cys Gly Thr Gly Glu Asp Tyr Cys Gly Ala Gly Cys
         40                  45                  50 cag tcg ggc ccc tgc gac gtg ccg gag acc aac aac gcg tcc gtg gcc      248
Gln Ser Gly Pro Cys Asp Val Pro Glu Thr Asn Asn Ala Ser Val Ala
 55                  60                  65 agc atc gtg acg ccg gcc ttc ttc gac gcg ctc ctc gcg cag gcc gcc      296
Ser Ile Val Thr Pro Ala Phe Phe Asp Ala Leu Leu Ala Gln Ala Ala
 70                  75                  80                  85 gcc tcg tgc gag gcc aac ggc ttc tac acc cgc gac gcc ttc ctc gcc      344
Ala Ser Cys Glu Ala Asn Gly Phe Tyr Thr Arg Asp Ala Phe Leu Ala
                 90                  95                 100 gcc gcc ggc tac tac ccg gcg ttc ggc cgc acc ggc acc gtc gac gac      392
Ala Ala Gly Tyr Tyr Pro Ala Phe Gly Arg Thr Gly Thr Val Asp Asp
            105                 110                 115 tcc aag cgc gag atc gcc gcc ttc ttc ggc aac gcc aac cac gag acc      440
Ser Lys Arg Glu Ile Ala Ala Phe Phe Gly Asn Ala Asn His Glu Thr
        120                 125                 130 ata a gtacgtgcga acaaaccgaa gctcgtccaa gctctagctg ctactaatca         494
Ile agtttcgact gctcgcag ag ttc tgc tac atc aac gag atc gac ggg ccg       544
                       Lys Phe Cys Tyr Ile Asn Glu Ile Asp Gly Pro
                           135                 140                 145 agc aag aac tac tgc gac cgg aac aac acg cag tgg ccg tgc cag gcg      592
Ser Lys Asn Tyr Cys Asp Arg Asn Asn Thr Gln Trp Pro Cys Gln Ala
                150                 155                 160 ggg aag ggg tac tac ggc cgc ggc ccg ctg cag atc tcc tgg aac ttc      640
Gly Lys Gly Tyr Tyr Gly Arg Gly Pro Leu Gln Ile Ser Trp Asn Phe
            165                 170                 175 aac tac ggg ccc gcg ggg cag agc atc ggc ttc gac ggg ctg ggc gac      688
Asn Tyr Gly Pro Ala Gly Gln Ser Ile Gly Phe Asp Gly Leu Gly Asp
        180                 185                 190 ccc gac gcg gtg gcg cgc agc gcc gtg ctc gcg ttc cgc tcc gcg ctc      736
Pro Asp Ala Val Ala Arg Ser Ala Val Leu Ala Phe Arg Ser Ala Leu
195                 200                 205 tgg tac tgg atg aac aac gtg cac ggg gcc atc gtc tcc ggc cag ggc      784
Trp Tyr Trp Met Asn Asn Val His Gly Ala Ile Val Ser Gly Gln Gly
210                 215                 220                 225 ttc ggc gcc acc atc cgg gcc atc aac ggc gcg ctc gag tgc gac ggc      832
Phe Gly Ala Thr Ile Arg Ala Ile Asn Gly Ala Leu Glu Cys Asp Gly
            230                 235                 240 aag aac ccc aac tcc gtc aac aac cgc gtc gcc tac tac aag cag ttc      880
Lys Asn Pro Asn Ser Val Asn Asn Arg Val Ala Tyr Tyr Lys Gln Phe
        245                 250                 255 tgc cag gat ttc ggc gtc gac ccg ggc aac aac ctc acc tgc                922
Cys Gln Asp Phe Gly Val Asp Pro Gly Asn Asn Leu Thr Cys
        260                 265                 270 tgaatgatct ctctctcatt gggttgttgt cctgtactta cacatgtgtt ggttgatgga    982
tagatggcga ttgcgtggtg cggatgtttc ggtttggcgg tgtcaattct gatatgcgcg    1042
tcggtgctgt tctgatactg actatatacg gaaataaaaa tctgatttgc attaaaaaaa    1102
aaaaaaaaaa aaaa                                                      1116

<210> SEQ ID NO 32
<211> LENGTH: 36
<212> TYPE: DNA
<213> ORGANISM: Artificial Sequence
<220> FEATURE:
```

```
<223> OTHER INFORMATION: Polynucleotide used for subtractive
      hybridization

<400> SEQUENCE: 32
tcgacccacg cgtccgaaaa aaaaaaaaaa aaaaaa                                    36
```